US011198726B2

(12) United States Patent
Hilberg et al.

(10) Patent No.: US 11,198,726 B2
(45) Date of Patent: Dec. 14, 2021

(54) ANTI-CANCER COMBINATION THERAPY

(71) Applicant: Boehringer Ingelheim International GmbH, Ingelheim am Rhein (DE)

(72) Inventors: Frank Hilberg, Vienna (AT); Marco Hans Hofmann, Vienna (AT); Markus Reschke, Birsfelden (CH); Flavio Solca, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 311 days.

(21) Appl. No.: 15/995,375

(22) Filed: Jun. 1, 2018

(65) Prior Publication Data

US 2018/0346559 A1 Dec. 6, 2018

(30) Foreign Application Priority Data

Jun. 2, 2017 (EP) .................................. 17174323
Oct. 17, 2017 (EP) .................................. 17196949

(51) Int. Cl.

| C07K 16/22 | (2006.01) |
|---|---|
| C07K 16/18 | (2006.01) |
| C07K 16/28 | (2006.01) |
| A61K 39/395 | (2006.01) |
| A61K 31/502 | (2006.01) |
| A61P 35/00 | (2006.01) |
| C07K 16/30 | (2006.01) |
| A61K 39/00 | (2006.01) |

(52) U.S. Cl.
CPC ............ C07K 16/22 (2013.01); A61K 31/502 (2013.01); A61K 39/39541 (2013.01); A61K 39/39558 (2013.01); A61P 35/00 (2018.01); C07K 16/18 (2013.01); C07K 16/2818 (2013.01); C07K 16/3023 (2013.01); *A61K 2039/505* (2013.01); *A61K 2039/507* (2013.01); *C07K 2317/22* (2013.01); *C07K 2317/24* (2013.01); *C07K 2317/31* (2013.01); *C07K 2317/565* (2013.01); *C07K 2317/569* (2013.01); *C07K 2317/76* (2013.01)

(58) Field of Classification Search
CPC ............ C07K 16/22; C07K 2317/22; C07K 2317/31; C07K 2317/565; C07K 2317/569; C07K 2317/76; A61K 39/39558; A61K 2039/507
USPC ............................................. 424/133.1, 136.1
See application file for complete search history.

(56) References Cited

U.S. PATENT DOCUMENTS

| 9,527,925 | B2 * | 12/2016 | Gschwind | ............... A61P 35/00 |
| 10,414,828 | B2 * | 9/2019 | Gschwind | ............. C07K 16/22 |
| 10,793,634 | B2 * | 10/2020 | Herrmann | ............... A61P 25/28 |
| 2013/0078248 | A1 * | 3/2013 | Gschwind | ................. A61P 5/00 424/136.1 |
| 2013/0259859 | A1 * | 10/2013 | Ott | ..................... A61K 39/3955 424/133.1 |
| 2014/0093498 | A1 * | 4/2014 | Gschwind | .......... A61K 38/1761 424/133.1 |
| 2014/0093499 | A1 * | 4/2014 | Gschwind | ............. C07K 16/22 424/133.1 |
| 2017/0107281 | A1 * | 4/2017 | Ott | ..................... C07K 16/3015 |
| 2017/0247475 | A1 * | 8/2017 | Gschwind | ............... A61P 27/02 |
| 2020/0010569 | A1 * | 1/2020 | Gschwind | ............ C07K 16/468 |

FOREIGN PATENT DOCUMENTS

| WO | 2010040508 A1 | 4/2010 |
| WO | 2012131078 A1 | 10/2012 |
| WO | 2016170039 | 10/2016 |
| WO | 2016170040 | 10/2016 |
| WO | 2017165681 | 9/2017 |
| WO | WO 2017/198741 | * 11/2017 |

OTHER PUBLICATIONS

Kovalchuk et al. (Clin Exp Metastasis (Sep. 12, 2020).*
Weber (Seminars in Oncology, vol. 37, No. 5, Oct. 2010, pp. 430-439).*
Zhuansun, Anti-PD-1/PD-Li antibody versus conventional chemotherpay for previously-treated, advanced non-small cell lung cancer: a meta-analysis of randomized controlled trials, Journal of Thoracic Disease, 2017, vol. 9, p. 655-665.
International Search Report and Written Opinion for PCT/EP2018064445 dated Jul. 26, 2018.
Topalian, Safety, Activity, and Immune Correaltes of Anti-PD-1 Antibody in Cancer, The New J. of Medicine, vol. 366, 2012.
Stancovski, Mechanistic aspects of the opposingeffects of monclonal antibodies, Proc. Natl. Sci, vol. 88, 1991.
Bas, A holistic Evaluation of Articles of PD-1, Cancer Informatics, vol. 18, 2019.

* cited by examiner

*Primary Examiner* — Lynn A Bristol
(74) *Attorney, Agent, or Firm* — Wendy M. Gombert

(57) ABSTRACT

The invention relates to the combined use of certain bispecific, VEGF and Ang2 binding molecules with PD1 antagonists for the treatment of cancer. It further relates to pharmaceutical compositions and kits comprising such binding molecules and antagonists.

6 Claims, 3 Drawing Sheets

Specification includes a Sequence Listing.

FIG. 1
A
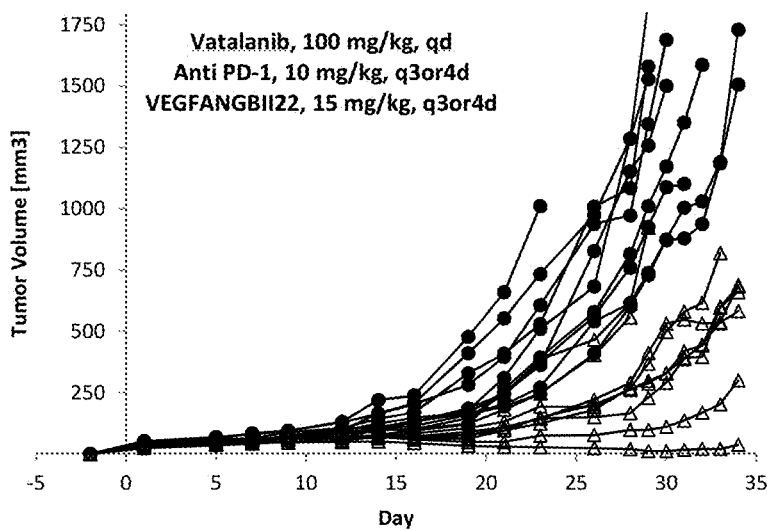
B
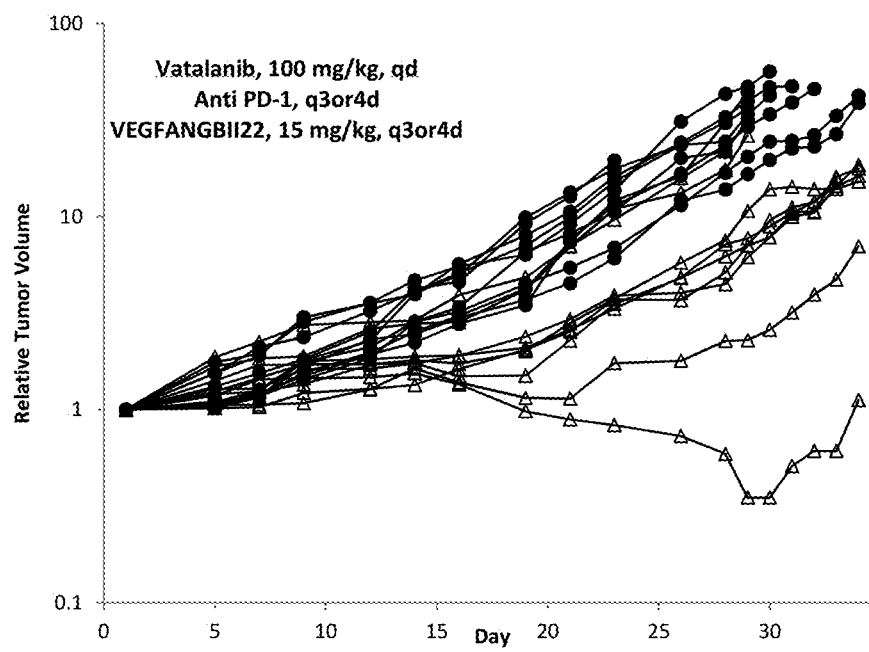
FIG. 1
/continued

C
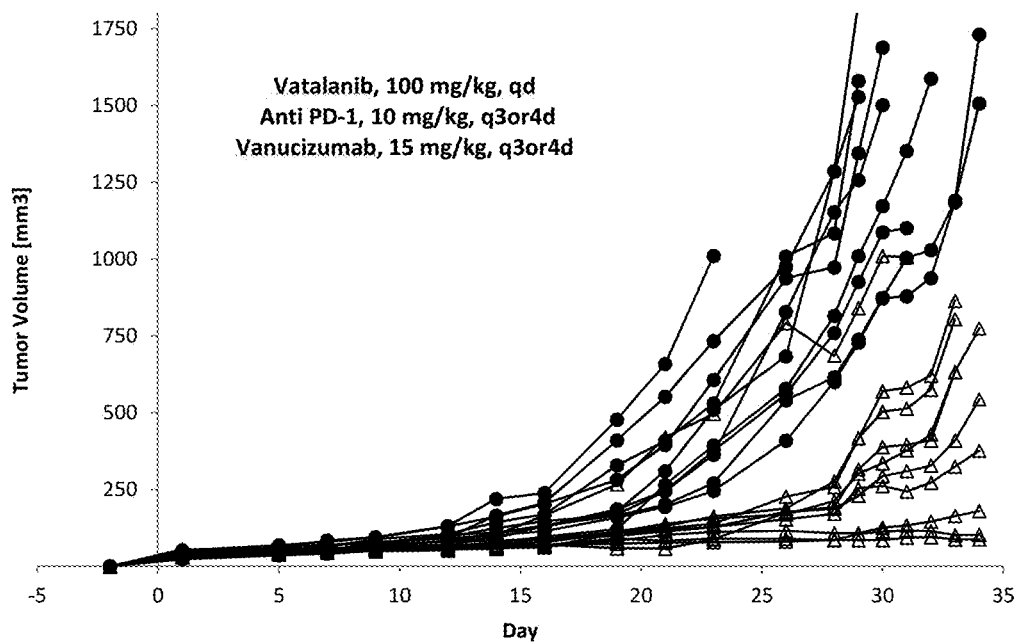
D
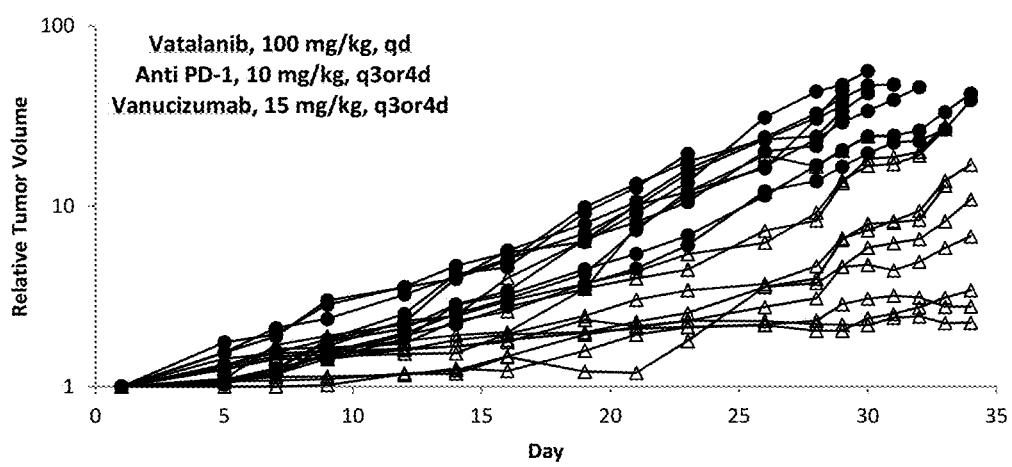

ANTI-CANCER COMBINATION THERAPY

FIELD OF THE INVENTION

The present invention relates to a combination therapy in the treatment of cancer and to compounds for use in such a combination therapy. The compounds for combination are a bispecific binding molecule, like an antibody derivative, and a PD-1 antagonist.

BACKGROUND OF THE INVENTION

Angiogenesis is the development of new blood vessels to provide a nutritive blood supply and a prerequisite for solid tumor growth and survival. Approaches in cancer therapy have been made in which key molecules involved in angiogenic pathways are targeted. These include modes of inhibition of the vascular endothelial growth factor (VEGF) signaling pathway as VEGF is considered the most potent angiogenic growth factor.

Lung cancer is the leading cause of cancer-related mortality with nearly 1.6 million deaths worldwide in 2012 or nearly 20% of cancer mortality as a whole (Molina et al., Mayo Clin Proc. 2008; 83(5):584-594; Chan et al., Transl Lung Cancer Res. 2014; 4(1):36-54). The most common type of lung cancer is the non-small cell lung cancer (NSCLC), which accounts for approximately 85% of all lung cancers (Chen et al. Nat Rev Cancer 2014; 14:535-546; Nawaz et al. Nat Rev Drug Discov. 2016; 15:229-230). NSCLC is nowadays understood as comprising a heterogeneous set of diseases having diverse pathophysiological characteristics, among them pulmonary adenocarcinoma, squamous-cell carcinoma (SCC) and large cell carcinoma as the most prominent subtypes.

In recent years, diverse new treatment options for patients with locally advanced or metastatic disease at the time of diagnosis in addition to chemotherapy and radiation therapy have been developed for cancer, especially for NSCLC. These new treatment methods are targeted therapies involving e g small molecule inhibitors or receptor monoclonal antibodies (mAb) and are based on alterations of the major cell-signaling and regulatory pathways—including alterations in receptor tyrosine kinases (TKs), such as epidermal growth factor receptor (EGFR), and alterations in angiogenic pathways—that are frequent in lung cancer. Much of recent work has focused on mutations of EGFR and on abnormal fusion of anaplastic lymphoma kinase (ALK) being inhibited by EGFR tyrosine kinase inhibitors and crizotinib. It has further been shown that combining the administration of the monoclonal antibody bevacizumab, which targets VEGF, with chemotherapy resulted in a significant improvement in survival among patients with colorectal cancer (Hurwitz et al. New Eng J Med 2004; 350:2335-2342) or advanced non-squamous NSCLC (Sandler et al. J Clin Oncol 2005 23(16s pt 1):2s). In addition to therapies of blocking components directly involved in the VEGF pathway, e.g. Angiopoietin2 (Ang2), a ligand of the Tie2 receptor tyrosine kinase controlling vascular remodeling by enabling the functions of other angiogenic factors, such as VEGF, has been another appealing target in cancer therapy.

WO2010/040508 and Kienast et al. (Clin Cancer Res; 19(24), 2013) disclose vanucizumab, a bispecific anti-VEGF/anti-Ang-2 antibody and its use in the treatment of cancer.

EP2694546 B1 and WO2012/131078 A1 relate to a bispecific binding molecule comprising a VEGF-binding immunoglobulin single variable domain and an Ang2-binding immunoglobulin single variable domain, and further a serum albumin binding immunoglobulin single variable domain that is used in the treatment of cancer and other diseases.

WO2016/170039 A1 relates to a combination therapy of an antibody specifically binding to Angiopoietin 2 with an antibody specifically binding to programmed death 1 polypeptide (PD-1).

WO2016/170040 A1 relates to a combination therapy of an antibody specifically binding to Angiopoietin 2 and an antibody specifically binding to VEGF with an antibody specifically binding to programmed death ligand 1 (PD-L1).

Despite all the approaches, there is still a need for improved treatment options for cancer patients. It is therefore an object of the present invention to provide pharmaceutical compositions and methods in cancer therapy for improved therapeutic efficacy and applicability.

BRIEF SUMMARY OF THE INVENTION

The present invention provides a method for treating a patient with a bispecific anti-VEGF/anti-Ang-2 antibody together with an antagonist against Programmed Death 1 (PD-1)—an immunoinhibitory protein that negatively regulates T cell receptor signals. The treatment leads to a significant reduction of tumor growth or even to tumor shrinkage (FIG. 1). Accordingly, the present invention provides a combination therapy comprising a bispecific anti-VEGF/anti-Ang-2 antibody and a PD-1 antagonist.

In a detailed aspect, the present invention relates to a method of treating and/or preventing an oncological or hyperproliferative disease, in particular cancer or a tumor disease, comprising administering to a patient in need thereof
a) a therapeutically effective amount of Compound A, and
b) a therapeutically effective amount of Compound B,
wherein
Compound A is a bispecific binding molecule comprising
a VEGF-binding immunoglobulin single variable domain,
a serum albumin binding immunoglobulin single variable domain, and
an Ang2-binding immunoglobulin single variable domain
wherein
said VEGF binding immunoglobulin single variable domain has the following CDR sequences:

```
CDR1:
                              (SEQ ID NO: 1)
SYSMG

CDR2:
                              (SEQ ID NO: 2)
AISKGGYKYDAVSLEG

CDR3:
                              (SEQ ID NO: 3)
SRAYGSSRLRLADTYEY
``` said serum albumin binding immunoglobulin single variable domain has the following CDR sequences:

```
CDR1:
                              (SEQ ID NO: 4)
SFGMS
```

```
CDR2:
                                      (SEQ ID NO: 5)
SISGSGSDTLYADSVKG

CDR3:
                                      (SEQ ID NO: 6)
GGSLSR,
``` said Ang2-binding immunoglobulin single variable domain has the following CDR sequences:

```
CDR1:
                                      (SEQ ID NO: 7)
DYAIG

CDR2:
                                      (SEQ ID NO: 8)
AIRSSGGSTYYADSVKG

CDR3:
                                      (SEQ ID NO: 9)
VPAGRLRYGEQWYPIYEYDA
```
and
wherein
Compound B is a PD-1 antagonist.

In a related aspect, the present invention provides a Compound A and Compound B, each for use in a method of treating and/or preventing an oncological or hyperproliferative disease, said method comprising administering Compound A and Compound B to a patient in need thereof.

The present invention further relates to the use of Compound A and Compound B, each for preparing a pharmaceutical composition for treating and/or preventing an oncological or hyperproliferative disease, wherein Compound A and Compound B, are intended for or provided for combined administration of Compound A and Compound B.

In another aspect, the present invention discloses a pharmaceutical composition comprising
a) Compound A and
b) Compound B
wherein
Compound A is a bispecific binding molecule comprising
  a VEGF-binding immunoglobulin single variable domain,
  a serum albumin binding immunoglobulin single variable domain, and
  an Ang2-binding immunoglobulin single variable domain,
wherein
  said VEGF binding immunoglobulin single variable domain has the following CDR sequences:

```
CDR1:
                                      (SEQ ID NO: 1)
SYSMG

CDR2:
                                      (SEQ ID NO: 2)
AISKGGYKYDAVSLEG

CDR3:
                                      (SEQ ID NO: 3)
SRAYGSSRLRLADTYEY
``` said serum albumin binding immunoglobulin single variable domain has the following CDR sequences:

```
CDR1:
                                      (SEQ ID NO: 4)
SFGMS

CDR2:
                                      (SEQ ID NO: 5)
SISGSGSDTLYADSVKG

CDR3:
                                      (SEQ ID NO: 6)
GGSLSR,
``` said Ang2-binding immunoglobulin single variable domain has the following CDR sequences:

```
CDR1:
                                      (SEQ ID NO: 7)
DYAIG

CDR2:
                                      (SEQ ID NO: 8)
AIRSSGGSTYYADSVKG

CDR3:
                                      (SEQ ID NO: 9)
VPAGRLRYGEQWYPIYEYDA
``` and
wherein
Compound B is a PD-1 antagonist.

In a further aspect, the present invention relates to a kit comprising
a) a first pharmaceutical composition comprising Compound A and
b) a second pharmaceutical composition comprising Compound B,
wherein Compound A and Compound B are defined as above.

DESCRIPTION OF THE FIGURES

FIG. 1 shows tumor growth inhibition upon treating 9 test individuals (open triangles, lower lines) with the bispecific binding molecule VEGFANGBII22 (compound A) (dose: 15 mg/kg; schedule: every 3-4 days) (A-B) and the CrossMab anti-VEGF/anti-Ang-2 antibody (vanucizumab) (dose: 15 mg/kg; schedule: every 3-4 days) as defined in WO2010/040508 or Kienast et al. (2013, supra) (C-D), respectively, in combination with the rat IgG2a anti-murine PD-1 antibody EX 101359 (clone RMP1-14) (dose: 10 mg/kg; schedule: every 3-4 days), as compared to 9 untreated individuals (filled circles, upper lines). Treated individuals were further administered with the small molecule tyrosine kinase inhibitor vatalanib (EXBF003) (dose: 100 mg/kg; schedule; once per day), to mimic anti-VEGF activity in mice models. Treatment started at day 5 after injection of $5 \times 10^4$ LL/2 subcutaneous tumor cells per mouse individual. Indicated are the tumor volume in mm$^3$ (A, C) and the corresponding randomized, relative tumor volume (B, D), respectively, until day 35 of the experiment.

DETAILED DESCRIPTION OF THE INVENTION

Figure 2:
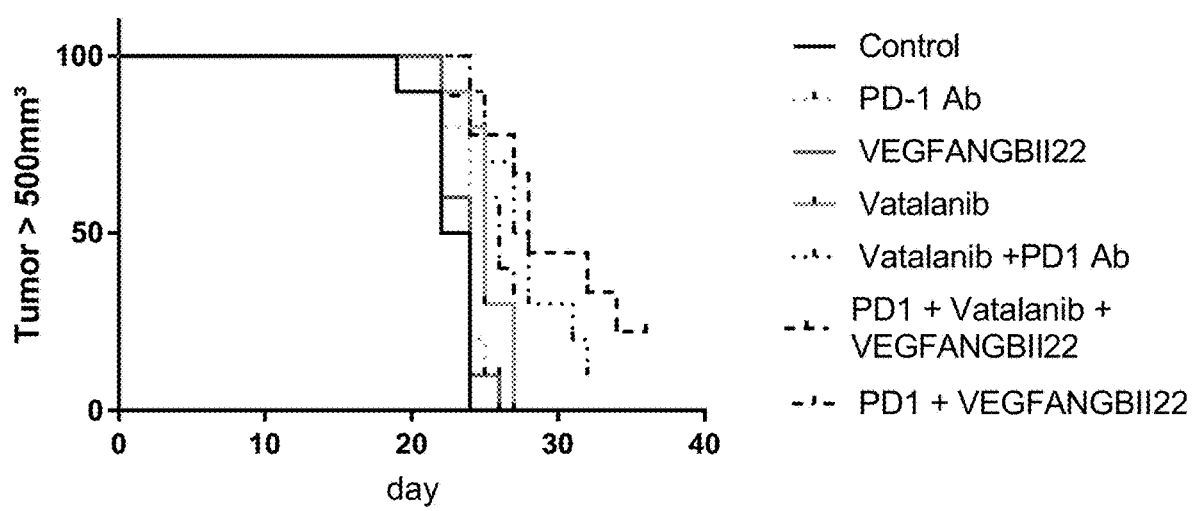
FIG. 2 shows mean survival of mice treated with control/Isotype antibody, anti-PD1 antibody (dose: 10 mg/kg; schedule: every 3-4 days), VEGFANGBII22 (dose: 15 mg/kg; schedule: every 3-4 days), vatalanib (dose: 100 mg/kg; schedule; once per day), vatalanib plus anti-PD1 antibody, vatalanib plus anti-PD1 antibody plus VEGFANGBII22, or anti-PD1 antibody plus VEGFANGBII22. Each treatment group consisted of 10 individual tumor bearing randomized mice. Treatment started at day 3 after injection of $5 \times 10^4$ LL/2 subcutaneous tumor cells per mouse individual.

The present invention relates to a method, compounds for use, use of compounds, pharmaceutical compositions and kits, all referring to the combined therapy or combined provision of Compound A and Compound B, wherein Compound A is a bispecific binding molecule comprising
  a VEGF-binding immunoglobulin single variable domain,
  a serum albumin binding immunoglobulin single variable domain, and
  an Ang2-binding immunoglobulin single variable domain
wherein
  said VEGF binding immunoglobulin single variable domain has the following CDR sequences:

```
CDR1:
                                         (SEQ ID NO: 1)
SYSMG

CDR2:
                                         (SEQ ID NO: 2)
AISKGGYKYDAVSLEG

CDR3:
                                         (SEQ ID NO: 3)
SRAYGSSRLRLADTYEY
``` said serum albumin binding immunoglobulin single variable domain has the following CDR sequences:

```
CDR1:
                                         (SEQ ID NO: 4)
SFGMS

CDR2:
                                         (SEQ ID NO: 5)
SISGSGSDTLYADSVKG

CDR3:
                                         (SEQ ID NO: 6)
GGSLSR,
``` said Ang2-binding immunoglobulin single variable domain has the following CDR sequences:

```
CDR1:
                                         (SEQ ID NO: 7)
DYAIG

CDR2:
                                         (SEQ ID NO: 8)
AIRSSGGSTYYADSVKG

CDR3:
                                         (SEQ ID NO: 9)
VPAGRLRYGEQWYPIYEYDA
``` and
wherein
  Compound B is a PD-1 antagonist.

The present inventors have surprisingly found that a combination of Compound A and Compound B results in a significant reduction, or even shrinkage, of tumor growth as compared to a therapy with Compound A only or Compound B only. Compound A and B work together synergistically and can lead to a reduction of cancer.

Compound A according to the present invention is a bispecific anti-VEGF/anti-Ang-2 binding molecule. Anti-angiogenesis therapies have become an important treatment option for several types of tumors. These therapies have focused on blocking the VEGF pathway (Ferrara et al., Nat Rev Drug Discov. 2004; 3(5):391-400) by neutralizing VEGF or its receptors. Recent studies in mice have shown that Angiopoietin2 (Ang2), a ligand of the Tie2 receptor, controls vascular remodeling by enabling the functions of other angiogenic factors, such as VEGF. Ang2 is primarily expressed by endothelial cells, strongly induced by hypoxia and other angiogenic factors and has been demonstrated to regulate tumor vessel plasticity, allowing vessels to respond to VEGF and FGF2 (Augustin et al., Nat Rev Mol Cell Biol. 2009; 10(3):165-77). Consistent with this role, the deletion or inhibition of Ang2 results in reduced angiogenesis (Gale et al., Dev Cell. 2002; 3(3):302-4) (Falcon et al., Am J Pathol. 2009; 175(5):2159-70). Elevated Ang2 serum concentrations have been reported for patients with colorectal cancer, NSCLC and melanoma (Goede et al., Br J Cancer. 2010 Oct. 26; 103(9):1407-14), (Park et al., Chest. 2007; 132(1): 200-6), (Helfrich et al., Clin Cancer Res. 2009 15; 15(4):1384-92). In CRC cancer Ang2 serum levels correlate with therapeutic response to anti-VEGF therapy.

Ang2 is a secreted, 66 kDa ligand for the Tie2 receptor tyrosine kinase (Augustin et al., Nat Rev Mol Cell Biol. 2009; 10(3):165-77). Ang2 consists of an N-terminal coiled-coil domain and a C-terminal fibrinogen-like domain, the latter is required for Tie2 interaction. Ang2 is primarily expressed by endothelial cells and strongly induced by hypoxia and other angiogenic factors, including VEGF. Tie2 is found on endothelial cells, haematopoietic stem cells and tumor cells. Ang2-Tie2 has been demonstrated to regulate tumor vessel plasticity, allowing vessels to respond to VEGF and FGF2.

The Ang-Tie system consists of 2 receptors (Tie1 and Tie2) and 3 ligands (Ang1, Ang2 and Ang4) (Augustin et al., Nat Rev Mol Cell Biol. 2009; 10(3):165-77). Tie2, Ang1 and Ang2 are the best studied members of this family, Tie1 is an orphan receptor and the role of Ang4 for vascular remodeling still needs to be defined. Ang2 and Ang1 mediate opposing functions upon Tie2 binding and activation. Ang2-mediated Tie2 activation results in endothelial cell activation, pericyte dissociation, vessel leakage and induction of vessel sprouting. In contrast to Ang2, Ang1 signaling maintains vessel integrity by recruitment of pericytes, thereby maintaining endothelial cell quiescence.

Bispecific anti-VEGF/anti-Ang-2 binding molecules that can be used according to the invention are e.g. disclosed in WO2012/131078, incorporated herein by reference).

Compound B according to the present invention is an antagonist against a member of the protein Programmed Death 1 (PD-1) family, such as PD-1 itself or one of its ligands, PD-L1 or PD-L2. PD-1 is known as an immunoinhibitory protein that negatively regulates TCR signals (Ishida, Y. et al. (1992) EMBO J. 11:3887-3895; Blank, C. et al. (2006) Immunol. Immunother. 56(6):739-745). The interaction between PD-1 and PD-L1 can act as an immune checkpoint, which can lead to, e.g., a decrease in tumor infiltrating lymphocytes, a decrease in T-cell receptor mediated proliferation, and/or immuno evasion by cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100) Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci USA 99:12293-7; Brown et al. (2003) J. Immunol. 170:1257-66).

PD-1 is an inhibitory member of the extended CD28/CTLA-4 family of T cell regulators. Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes (Okazaki et al. (2002) Curr Opin Immunol 14:391779-82; Bennett et al. (2003) J. Immunol. 170:711-8). Two ligands for PD-1 have been identified, PD-L1 (B7-H1) and PD-L2 (B7-DC), that have been shown to downregulate T cell activation upon binding to PD-1 (Freeman et al. (2000) J. Exp. Med. 192:1027-34; Carter et al. (2002) Eur. J. Immunol. 32:634-43). Both PD-L1 and PD-L2 are B7 homologs that bind to PD-1. PD-L1 is abundant in a variety of human cancers (Dong et al. (2002) Nat. Med. 8:787-9).

The PD-1 gene encodes a 55 kDa type I transmembrane protein that is part of the Ig gene superfamily (Agata et al. (1996) Int Immunol. 8:765-72). The complete PD-1 sequence can be found under GenBank Accession No. U64863. Although structurally similar to CTLA-4, PD-1 lacks the MYPPY motif (SEQ ID NO: 10) that is important for B7-1 and B7-2 binding.

In view of the above, monoclonal antibodies as PD-1 antagonists have been developed in recent years for use in therapy, more precisely for treating various diseases, including cancer and infectious diseases (e.g., WO2006/121168; WO2015/112900). Any one of such antibodies can be used according to the present invention.

The present inventors have surprisingly found that treating individuals with a combination of Compound A and Compound B as defined above/below leads to a significant stronger reduction—or even shrinkage—in tumor volume as compared to treatment with Compound A only or Compound B only. Moreover, when compared to a treatment of individuals with vanucizumab and the same PD-1 antagonist, treatment with a composition comprising Compound A and Compound B as defined above/below even resulted in tumor shrinkage (Example 1; FIG. 1). Both Compound A and Compound B are active agents according to the present invention.

A PD-1 antagonist within the meaning of this invention is a compound that inhibits the interaction of PD-1 with its receptor(s) or ligand(s).

Preferably, the PD-1 antagonist is an inhibitor of PD-1 or an inhibitor of PD-L1. The PD-1 antagonist may preferably be an anti-PD-1-antibody or an anti-PD-L1-antibody, and more preferably a humanized or fully human anti-PD-1 antibody or a humanized or fully human anti-PD-L1 antibody. Any one of these antibodies may be a recombinant human antibody.

The term "antibody" herein is used in the broadest sense and encompasses various antibody structures, including but not limited to monoclonal antibodies, polyclonal antibodies, multispecific antibodies (e.g. bispecific antibodies), single chain antibodies, single domain antibodies, and fragmented antibodies (also referred to as antibody fragments), such as Fab, F(ab)$_2$, F(ab')$_2$, Fab', single chain variable-fragments (scFv) or antigen binding domains of an antibody, so long as they exhibit the desired antigen-binding activity.

The antibody may have an effector function, such as ADCC or CDC, that is usually mediated by the Fc part (antibody constant region) of the antibody, or it may have no effector function, e.g. by lacking a Fc part or having a blocked, masked Fc part, in essence a Fc part that is not or insufficiently recognized by immune cells or immune system components, like the complement system.

The antibody or its fragment may be of any type, e.g. IgA, IgD, IgE, IgG, IgM. Preferred is IgG.

The terms "monoclonal antibody" or "monoclonal antibody composition" as used herein refer to a preparation of antibody molecules of a single amino acid composition.

A "recombinant antibody" is an antibody which has been produced by a recombinantly engineered host cell. It is optionally isolated or purified.

A "human antibody" is one which possesses an amino acid sequence which corresponds to that of an antibody produced by a human cell or derived from a non-human source that utilizes human antibody repertoires or other human antibody-encoding sequences. This definition of a human antibody specifically excludes a humanized antibody comprising non-human antigen-binding residues.

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "humanized" antibody refers to a chimeric antibody comprising amino acid residues from non-human hypervariable regions (HVRs) and amino acid residues from human FRs. In certain embodiments, a humanized antibody will comprise substantially all of at least one, and typically two, variable domains, in which all or substantially all of the HVRs (e.g. complementary determining regions (CDRs)) correspond to those of a non-human antibody, and all or substantially the entire framework regions (FRs) correspond to those of a human antibody. A humanized antibody optionally may comprise at least a portion of an antibody constant region derived from a human antibody. A "humanized form" of an antibody, e.g. a non-human antibody, refers to an antibody that has undergone humanization.

"Binding" of a polypeptide (such as an immunoglobulin, an antibody, an immunoglobulin single variable domain of the invention, or generally an antigen-binding molecule or a fragment thereof) means "having affinity for" or "having specificity for" a certain epitope, antigen or protein (or for at least one part, fragment or epitope thereof).

Generally, the term "specificity" refers to the number of different types of antigens or epitopes to which a particular antigen-binding molecule or antigen-binding protein (such as an immunoglobulin single variable domain of the invention) molecule can bind. The specificity of antigen-binding molecule can be determined based on its affinity and/or avidity. The affinity, represented by the equilibrium constant for the dissociation of an antigen with an antigen-binding protein (KD), is a measure for the binding strength between an epitope and an antigen-binding site on the antigen-binding protein: the lesser the value of the KD, the stronger the binding strength between an epitope and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin, an antibody, an immunoglobulin single variable domain or a polypeptide) containing it and the pertinent antigen. Avidity is related to both the affinity between an epitope and its antigen binding site on the antigen-binding molecule and the number of pertinent binding sites present on the antigen-binding molecule.

Natural antibodies, for example, are monospecific. The term "monospecific antibody" as used herein denotes an antibody that has one or more binding sites each of which bind to the same epitope of the same antigen. "Multispecific antibodies" bind two or more different epitopes (for example, two, three, four, or more different epitopes). The epitopes may be on the same or different antigens. An example of a multispecific antibody is a "bispecific antibody" which binds two different epitopes. When an antibody possesses more than one specificity, the recognized epitopes may be associated with a single antigen or with more than one antigen.

An epitope is a region of an antigen that is bound by an antibody or antigen binding moiety. The term "epitope" includes any polypeptide determinant capable of specific binding to an antibody or antigen binding moiety. In certain embodiments, epitope determinants include chemically active surface groupings of molecules such as amino acids, glycan side chains, phosphoryl, or sulfonyl, and, in certain embodiments, may have specific three dimensional structural characteristics, and/or specific charge characteristics. Conformational and non-conformational epitopes are distinguished in that the binding to the former but not the latter is lost in the presence of denaturing solvents. As used herein, the terms "binding" and "specific binding" refer to the binding of the antibody or antigen binding moiety to an epitope of the antigen in an in vitro assay, preferably in a plasmon resonance assay (BIAcore®, GE-Healthcare Uppsala, Sweden) with purified wild-type antigen.

The affinity of the binding of the binding molecules (e.g. antibodies) according to the present invention, including antibodies thereof of Compound A or Compound B, to an antigen is defined by the terms $k_a$ (rate constant for the association of the antibody from the antibody/antigen complex), $k_D$ (dissociation constant), and $K_D$ (kD/ka). In one embodiment binding or that/which specifically binds to means a binding affinity ($K_D$) of $10^{-8}$ mol/l or less, in one embodiment $10^{-8}$ M to $10^{-13}$ mol/l. Thus, an multispecific antibody according to the invention specifically binds to each antigen for which it is specific with a binding affinity ($K_D$) of $10^{-8}$ mol/l or less, e.g. with a binding affinity ($K_D$) of $10^{-8}$ to $10^{-13}$ mol/l. In one embodiment, with a binding affinity ($K_D$) is $10^{-9}$ to $10^{-13}$ mol/l.

The expressions "variable domains" or "variable region" or Fv as used herein denotes each of the pair of light and heavy chains which is involved directly in binding the antibody to the antigen. The variable domain of a light chain is abbreviated as "VL" and the variable domain of a heavy chain is abbreviated as "VH". The variable light and heavy chain domains have the same general structure and each domain comprises four framework (FR) regions whose sequences are widely conserved, connected by three HVRs (or CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "constant domains" or "constant region" as used within the current application denotes the sum of the domains of an antibody other than the variable region. The constant region is not directly involved in binding of an antigen, but exhibits various effector functions.

The "constant domains" as used in the antibodies disclosed herein are preferably from human origin, which is from a constant heavy chain region of a human antibody of the subclass IgG1, IgG2, IgG3, or IgG4 and/or a constant light chain kappa or lambda region. Such constant domains and regions are well known in the state of the art and e.g. described by Kabat et al. ("Sequence of proteins of immunological interest", US Public Health Services, NIH Bethesda, Md., Publication No. 91).

The "Fc part" of an antibody is not involved directly in binding of an antibody to an antigen, but exhibits various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al, Nature 282 (1979) 742-743; Lukas, T. J., et al, J. Immunol. 127 (1981) 2555-2560; Brunhouse, R., and Cebra, J. J., Mol. Immunol. 16 (1979) 907-917; Burton, D. R., et al, Nature 288 (1980) 338-344; Thommesen, J. E., et al, Mol. Immunol. 37 (2000) 995-1004; Idusogie, E. E., et al, J. Immunol. 164 (2000) 4178-4184; Hezareh, M., et al, J. Virology 75 (2001) 12161-12168; Morgan, A., et al, Immunology 86 (1995) 319-324; EP 0307434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

Regarding Compound A, the term "bispecific binding molecule" refers to a molecule comprising at least one Ang2-binding molecule (or "Ang2-binding component") and at least one VEGF-binding molecule (or "VEGF-binding component"). A bispecific binding molecule may contain more than one Ang2-binding molecule and/or more than one VEGF-binding molecule, i.e. in the case that the bispecific binding molecule contains a biparatopic (as defined below) Ang2-binding molecule and/or a biparatopic VEGF-binding molecule, in part of the molecule that binds to Ang2 or to VEGF, i.e. in its "Ang2-binding component" (or anti-Ang2 component) or "VEGF-binding component" (or anti-VEGF component), respectively. The word "bispecific" in this context is however not to be construed as to exclude further binding components with binding specificity to molecules other than VEGF and Ang2 from the bispecific binding molecule. Non-limiting examples of such further binding components are binding components binding to serum albumin.

Unless indicated otherwise, the term "VEGF-binding molecule" or "Ang2-binding molecule" includes anti-VEGF or anti-Ang2 antibodies, anti-VEGF antibody or anti-Ang2 antibody fragments", "anti-VEGF antibody-like molecules" or "anti-Ang2 antibody-like molecules", as defined herein, and conjugates with any of these. Antibodies include, but are not limited to, monoclonal and chimerized monoclonal antibodies. The term "antibody" encompasses complete immunoglobulins, like monoclonal antibodies produced by recombinant expression in host cells, as well as antibody fragments or "antibody-like molecules", including single-chain antibodies and linear antibodies, so-called "SMIPs" ("Small Modular Immunopharmaceuticals"), as e.g. described in WO2002/056910; Antibody-like molecules include immunoglobulin single variable domains, as defined herein. Other examples for antibody-like molecules are immunoglobulin super family antibodies (IgSF), or CDR-grafted molecules.

"Ang2-binding molecule" or "VEGF-binding molecule" respectively, refers to both monovalent target-binding molecules (i.e. molecules that bind to one epitope of the respective target) as well as to bi- or multivalent binding molecules (i.e. binding molecules that bind to more than one epitope, e.g. "biparatopic" molecules as defined hereinbelow). Ang2 (or VEGF)-binding molecules containing more than one Ang2 (or VEGF)-binding immunoglobulin single variable domain are also termed "formatted" binding molecules, they may, within the target-binding component, in addition to the immunoglobulin single variable domains, comprise linkers and/or moieties with effector functions, e.g. half-life-extending moieties like albumin-binding immunoglobulin single variable domains, and/or a fusion partner like serum albumin and/or an attached polymer like PEG.

The term "biparatopic Ang2 (or VEGF)-binding molecule" or "biparatopic immunoglobulin single variable domain" as used herein shall mean a binding molecule comprising a first immunoglobulin single variable domain and a second immunoglobulin single variable domain as defined herein, wherein the two molecules bind to two non-overlapping epitopes of the respective antigen. The biparatopic binding molecules are composed of immunoglobulin single variable domains which have different specificities with respect to the epitope.

A formatted binding molecule may, albeit less preferred, also comprise two identical immunoglobulin single variable domains or two different immunoglobulin single variable domains that recognize the same or overlapping epitopes or their respective antigen. In this case, with respect to VEGF, the two immunoglobulin single variable domains may bind to the same or an overlapping epitope in each of the two monomers that form the VEGF dimer.

The efficacy of the bispecific binding molecule of the invention, and of compositions comprising the same, can be tested using any suitable in vitro assay, cell-based assay, in vivo assay and/or animal model known per se, or any combination thereof, depending on the specific disease or disorder of interest. Suitable assays and animal models will be clear to the skilled person, and for example include the assays described in EP 2694546 B1.

Unless indicated otherwise, the terms "immunoglobulin" and "immunoglobulin sequence"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence") should generally be understood to include both the relevant amino acid sequence as well as nucleic acid sequences or nucleotide sequences encoding the same, unless the context requires a more limited interpretation.

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin the immunoglobulin fold characteristic of antibody molecules, which consists of a 2-layer sandwich of about 7 antiparallel beta-strands arranged in two beta-sheets, optionally stabilized by a conserved disulphide bond. An immunoglobulin domain comprises (a) variable domain(s), i.e. one or more immunoglobulin variable domains.

The term "immunoglobulin variable domain" as used herein means an immunoglobulin domain essentially consisting of four "framework regions" which are referred to in the art and hereinbelow as "framework region 1" or "FR1"; as "framework region 2" or "FR2"; as "framework region 3" or "FR3"; and as "framework region 4" or "FR4", respectively; which framework regions are interrupted by three "complementary determining regions" or "CDRs", which are referred to in the art and hereinbelow as "complementary determining region 1" or "CDR1"; as "complementary determining region 2" or "CDR2"; and as "complementary determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site. The molecules of the present invention include immunoglobulin single variable domains like VHHs.

The term "immunoglobulin single variable domain" as used herein means an immunoglobulin variable domain which is capable of specifically binding to an epitope of the antigen without pairing with an additional variable immunoglobulin domain. One example of immunoglobulin single variable domains in the meaning of the present invention are "domain antibodies", such as the immunoglobulin single variable domains VH and VL (VH domains and VL domains). Another example of immunoglobulin single variable domains are "VHH domains" (or simply "VHHs") from camelids, as described hereinafter.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e. by a VH-VL pair of immunoglobulin domains, which jointly bind to an epitope of the respective antigen.

"VHH domains", also known as VHHs, $V_HH$ domains, VHH antibody fragments, and VHH antibodies, have originally been described as the antigen binding immunoglobulin (variable) domain of "heavy chain antibodies" (i.e. of "antibodies devoid of light chains"; Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "VL domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms VHH domain, VHH, $V_HH$ domain, VHH antibody fragment, VHH antibody are used interchangeably and are representatives of immunoglobulin single variable domains (having the structure FR1-CDR1-FR2-CDR2-FR3-CDR3-FR4 and specifically binding to an epitope without requiring the presence of a second immunoglobulin variable domain), and which are distinguished from VH domains by the so-called "hallmark residues", as defined in e.g. WO 2009/109635, FIG. 1.

The amino acid residues of a immunoglobulin single variable domain, e.g. a VHH, are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans, J. Immunol. Methods 231, 25-38 (1999). According to this numbering
 FR1 comprises the amino acid residues at positions 1-30,
 CDR1 comprises the amino acid residues at positions 31-35,
 FR2 comprises the amino acids at positions 36-49,
 CDR2 comprises the amino acid residues at positions 50-65,
 FR3 comprises the amino acid residues at positions 66-94,
 CDR3 comprises the amino acid residues at positions 95-102, and
 FR4 comprises the amino acid residues at positions 103-113.

However, it should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain one or more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of $V_H$ domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Immunoglobulin single variable domains, e.g. VHHs and domain antibodies, according to the preferred embodiments of the invention, have a number of unique structural characteristics and functional properties which makes them highly advantageous for use in therapy as functional antigen-binding molecules. In particular, and without being limited thereto, VHH domains (which have been "designed" by nature to functionally bind to an antigen without pairing with a light chain variable domain) can function as single, relatively small, functional antigen-binding structural units.

Further details and information about advantages of immunoglobulin single variable domains and about obtaining VHHs are disclosed in detail in EP 2694546 B1.

The immunoglobulin single variable domains of the invention are not limited with respect to a specific biological source from which they have been obtained or to a specific method of preparation. Suitable methods and techniques for obtaining VHH domains binding to a specific antigen or epitope have been described in WO2006/040153 and WO2006/122786.

According to specific embodiments, the immunoglobulin single variable domains of the invention are VHH domains with an amino acid sequence that essentially corresponds to the amino acid sequence of a naturally occurring VHH domain, but that has been "humanized" or "sequence-optimized" (optionally after affinity-maturation), i.e. by replacing one or more amino acid residues in the amino acid sequence of said naturally occurring VHH sequence by one or more of the amino acid residues that occur at the corresponding position(s) in a variable heavy domain of a conventional 4-chain antibody from a human being. This can be performed using methods known in the art, which can be routinely used by the skilled person.

A humanized VHH domain may contain one or more fully human framework region sequences, and, in an even more specific embodiment, may contain human framework region sequences derived from the human germline Vh3 sequences DP-29, DP-47, DP-51, or parts thereof, or be highly homologous thereto, optionally combined with JH sequences, such as JH5. Thus, a humanization protocol may comprise the replacement of any of the VHH residues with the corresponding framework 1, 2 and 3 (FR1, FR2 and FR3) residues of germline VH genes such as DP 47, DP 29 and DP 51) either alone or in combination. Suitable framework regions (FR) of the immunoglobulin single variable domains of the invention can be selected from those as set out e.g. in WO 2006/004678 and specifically include the so-called "KERE" and "GLEW" classes. Examples are immunoglobulin single variable domains having the amino acid sequence G-L-E-W at about positions 44 to 47, and their respective humanized counterparts. A humanized VHH domain may contain one or more fully human framework region sequences.

By way of example, a humanizing substitution for VHHs belonging to the 103 P,R,S-group and/or the GLEW-group (as defined below) is 108Q to 108L. Methods for humanizing immunoglobulin single variable domains are known in the art.

Binding immunoglobulin single variable domains with improved properties in view of therapeutic application, e.g. enhanced affinity or decreased immunogenicity, may be obtained from individual binding molecules by techniques known in the art, such as affinity maturation (for example, starting from synthetic, random or naturally occurring immunoglobulin sequences), CDR grafting, humanizing, combining fragments derived from different immunoglobulin sequences, PCR assembly using overlapping primers, and similar techniques for engineering immunoglobulin sequences well known to the skilled person; or any suitable combination of any of the foregoing, also termed "sequence optimization", as described herein. Reference is, for example, made to standard handbooks, as well as to the further description and Examples.

In accordance with the above, in a preferred embodiment, the immunoglobulin single variable domains of Compound A are VHH domains. More preferably, Compound A is selected from compounds having the following amino acid sequences:

(SEQ ID NO: 11)
DVQLVESGGGLVQPGGSLRLSCAASGRTFSSYSMGWFRQAPGKEREF

VVAISKGGYKYDAVSLEGRFTISRDNAKNTVYLQINSLRPEDTAVYY

CASSRAYGSSRLRLADTYEYWGQGTLVTVSSGGGGSGGGSEVQLVES

GGGLVQPGNSLRLSCAASGFTFSSFGMSWVRQAPGKGLEWVSSISGS

GSDTLYADSVKGRFTISRDNAKTTLYLQMNSLRPEDTAVYYCTIGGS

LSRSSQGTLVTVSSGGGGSGGGSEVQLVESGGGLVQPGGSLRLSCAV

SGITLDDYAIGWFRQAPGKEREGVSAIRSSGGSTYYADSVKGRFTIS

SDNSKNTVYLQMNSLRPEDTAVYYCAAVPAGRLRYGEQWYPIYEYDA

WGQGTLVTVSS;

(SEQ ID NO: 12)
EVQLVESGGGLVQPGGSLRLSCAASGRTFSSYSMGWFRQAPGKEREF

VVAISKGGYKYDAVSLEGRFTISRDNAKNTVYLQINSLRPEDTAVYY

CASSRAYGSSRLRLADTYEYWGQGTLVTVSSGGGGSGGGSEVQLVES

GGGLVQPGNSLRLSCAASGFTFSSFGMSWVRQAPGKGLEWVSSISGS

GSDTLYADSVKGRFTISRDNAKTTLYLQMNSLRPEDTAVYYCTIGGS

LSRSSQGTLVTVSSGGGGSGGGSEVQLVESGGGLVQPGGSLRLSCAV

SGITLDDYAIGWFRQAPGKEREGVSAIRSSGGSTYYADSVKGRFTIS

SDNSKNTVYLQMNSLRPEDTAVYYCAAVPAGRLRYGEQWYPIYEYDA

WGQGTLVTVSS;
and (SEQ ID NO: 13)
VQLVESGGGLVQPGGSLRLSCAASGRTFSSYSMGWFRQAPGKEREFV

VAISKGGYKYDAVSLEGRFTISRDNAKNTVYLQINSLRPEDTAVYYC

ASSRAYGSSRLRLADTYEYWGQGTLVTVSSGGGGSGGGSEVQLVESG

GGLVQPGNSLRLSCAASGFTFSSFGMSWVRQAPGKGLEWVSSISGSG

SDTLYADSVKGRFTISRDNAKTTLYLQMNSLRPEDTAVYYCTIGGSL

SRSSQGTLVTVSSGGGGSGGGSEVQLVESGGGLVQPGGSLRLSCAVS

GITLDDYAIGWFRQAPGKEREGVSAIRSSGGSTYYADSVKGRFTISS

DNSKNTVYLQMNSLRPEDTAVYYCAAVPAGRLRYGEQWYPIYEYDAW

GQGTLVTVSS.

The three sequences shown above are almost identical, except for the N-terminal sequence, which can be changed or modified in order to optimally adapt the sequence to the selected expression system (expression vector, host cell) or because of other needs. Thus, it is clear to the skilled person that further polypeptides which essentially comprise the above sequence, but which are slightly modified, e.g. by amino acid exchanges, deletions or additions which do not change the binding affinities of the resulting polypeptides, will also be useful as a "Compound A" of a pharmaceutical combination according to the invention.

In another embodiment, the representatives of the class of VEGF- and/or Ang2-binding immunoglobulin single variable domains of the invention have amino acid sequences that correspond to the amino acid sequence of a naturally occurring VH domain that has been "camelized", i.e. by replacing one or more amino acid residues in the amino acid sequence of a naturally occurring variable heavy chain from a conventional 4-chain antibody by one or more amino acid residues that occur at the corresponding position(s) in a VHH domain of a heavy chain antibody. This can be performed in a manner known per se, which will be clear to the skilled person, and reference is additionally be made to WO1994/04678. Such camelization may preferentially occur at amino acid positions which are present at the VH-VL interface and at the so-called Camelidae Hallmark residues (see for example also WO1994/04678). A detailed description of such "humanization" and "camelization" techniques and preferred framework region sequences consistent therewith can additionally be taken from e.g. pp. 98 of WO2006/040153 and pp. 107 of WO2006/122786.

A PD-1 antagonist within the meaning of this invention and all of its embodiments is a compound that inhibits the interaction of PD-1 with its receptor(s). PD-1 antagonists are well-known in the art, e.g. reviewed by Li et al., Int. J. Mol. Sci. 2016, 17, 1151 (incorporated herein by reference). Any PD-1 antagonist, especially antibodies, such as those disclosed by Li et al. as well as the further antibodies disclosed herein below, can be used according to the invention. Preferably, the PD-1 antagonist of this invention and all its embodiments is selected from the group consisting of the following antibodies:

pembrolizumab (anti-PD-1 antibody);
nivolumab (anti-PD-1 antibody);
pidilizumab (anti-PD-1 antibody);
PDR-001 (anti-PD-1 antibody);
PD1-1, PD1-2, PD1-3, PD1-4, and PD1-5 as disclosed herein below (anti-PD-1 antibodies)
atezolizumab (anti-PD-L1 antibody);
avelumab (anti-PD-L1 antibody);
durvalumab (anti-PD-L1 antibody).

Pembrolizumab (formerly also known as lambrolizumab; trade name Keytruda; also known as MK-3475) disclosed e.g. in Hamid, O. et al. (2013) New England Journal of Medicine 369(2):134-44, is a humanized IgG4 monoclonal antibody that binds to PD-1; it contains a mutation at C228P designed to prevent Fc-mediated cytotoxicity. Pembrolizumab is e.g. disclosed in U.S. Pat. No. 8,354,509 and WO2009/114335. It is approved by the FDA for the treatment of patients suffering from unresectable or metastatic melanoma and patients with metastatic NSCLC.

Nivolumab (CAS Registry Number: 946414-94-4; BMS-936558 or MDX1106b) is a fully human IgG4 monoclonal antibody which specifically blocks PD-1, lacking detectable antibody-dependent cellular toxicity (ADCC). Nivolumab is e.g. disclosed in U.S. Pat. No. 8,008,449 and WO2006/121168. It has been approved by the FDA for the treatment of patients suffering from unresectable or metastatic melanoma, metastatic NSCLC and advanced renal cell carcinoma.

Pidilizumab (CT-011; Cure Tech) is a humanized IgG1k monoclonal antibody that binds to PD-1. Pidilizumab is e.g. disclosed in WO 2009/101611.

PDR-001 or PDR001 is a high-affinity, ligand-blocking, humanized anti-PD-1 IgG4 antibody that blocks the binding of PD-L1 and PD-L2 to PD-1. PDR-001 is disclosed in WO2015/112900 and WO2017/019896.

Antibodies PD1-1 to PD1-5 are antibody molecules defined by the sequences as shown in Table 1, wherein HC denotes the (full length) heavy chain and LC denotes the (full length) light chain:

TABLE 1

| SEQ ID NO: | Sequence name | Amino acid sequence |
|---|---|---|
| 14 | HC of PD1-1 | EVMLVESGGGLVQPGGSLRLSCTASGFTFSASA MSWVRQAPGKGLEWVAYISGGGGDTYYSSSVKG RFTISRDNAKNSLYLQMNSLRAEDTAVYYCARH SNVNYYAMDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLG |
| 15 | LC of PD1-1 | EIVLTQSPATLSLSPGERATMSCRASENIDTSG ISFMNWYQQKPGQAPKLLIYVASNQGSGIPARF SGSGSGTDFTLTISRLEPEDFAVYYCQQSKEVP WTFGQGTKLEIKRTVAAPSVFIFPPSDEQLKSG TASVVCLLNNFYPREAKVQWKVDNALQSGNSQE SVTEQDSKDSTYSLSSTLTLSKADYEKHKVYAC EVTHQGLSSPVTKSFNRGEC |
| 16 | HC of PD1-2 | EVMLVESGGGLVQPGGSLRLSCTASGFTFSASA MSWVRQAPGKGLEWVAYISGGGGDTYYSSSVKG RFTISRDNAKNSLYLQMNSLRAEDTAVYYCARH SNPNYYAMDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLG |
| 17 | LC of PD1-2 | EIVLTQSPATLSLSPGERATMSCRASENIDTSG ISFMNWYQQKPGQAPKLLIYVASNQGSGIPARF SGSGSGTDFTLTISRLEpEDFAVYYCQQSKEVP WTFGQGTKLEIKRTVAAPSVFIFPPSDEQLKSG TASVVCLLNNFYPREAKVQWKVDNALQSGNSQE SVTEQDSKDSTYSLSSTLTLSKADYEKHKVYAC EVTHQGLSSPVTKSFNRGEC |
| 18 | HC of PD1-3 | EVMLVESGGGLVQPGGSLRLSCTASGFTFSKSA MSWVRQAPGKGLEWVAYISGGGGDTYYSSSVKG RFTISRDNAKNSLYLQMNSLRAEDTAVYYCARH SNVNYYAMDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLG |
| 19 | LC of PD1-3 | EIVLTQSPATLSLSPGERATMSCRASENIDVSG ISFMNWYQQKPGQAPKLLIYVASNQGSGIPARF SGSGSGTDFTLTISRLEPEDFAVYYCQQSKEVP WTFGQGTKLEIKRTVAAPSVFIFPPSDEQLKSG TASVVCLLNNFYPREAKVQWKVDNALQSGNSQE SVTEQDSKDSTYSLSSTLTLSKADYEKHKVYAC EVTHQGLSSPVTKSFNRGEC |
| 20 | HC of PD1-4 | EVMLVESGGGLVQPGGSLRLSCTASGFTFSKSA MSWVRQAPGKGLEWVAYISGGGGDTYYSSSVKG RFTISRDNAKNSLYLQMNSLRAEDTAVYYCARH SNVNYYAMDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLG |
| 21 | LC of PD1-4 | EIVLTQSPATLSLSPGERATMSCRASENIDVSG ISFMNWYQQKPGQAPKLLIYVASNQGSGIPARF SGSGSGTDFTLTISRLEPEDFAVYYCQQSKEVP WTFGQGTKLEIKRTVAAPSVFIFPPSDEQLKSG TASVVCLLNNFYPREAKVQWKVDNALQSGNSQE SVTEQDSKDSTYSLSSTLTLSKADYEKHKVYAC EVTHQGLSSPVTKSFNRGEC |
| 22 | HC of PD1-5 | EVMLVESGGGLVQPGGSLRLSCTASGFTFSKSA MSWVRQAPGKGLEWVAYISGGGGDTYYSSSVKG RFTISRDNAKNSLYLQMNSLRAEDTAVYYCARH SNVNYYAMDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLG |
| 23 | LC of PD1-5 | EIVLTQSPATLSLSPGERATMSCRASENIDVSG ISFMNWYQQKPGQAPKLLIYVASNQGSGIPARF SGSGSGTDFTLTISRLEPEDFAVYYCQQSKEVP WTFGQGTKLEIKRTVAAPSVFIFPPSDEQLKSG TASVVCLLNNFYPREAKVQWKVDNALQSGNSQE SVTEQDSKDSTYSLSSTLTLSKADYEKHKVYAC EVTHQGLSSPVTKSFNRGEC |

Specifically, the anti-PD-1 antibody molecule described herein above has:
(PD1-1:) a heavy chain comprising the amino acid sequence of SEQ ID NO:14 and a light chain comprising the amino acid sequence of SEQ ID NO:15; or
(PD1-2:) a heavy chain comprising the amino acid sequence of SEQ ID NO:16 and a light chain comprising the amino acid sequence of SEQ ID NO:17; or
(PD1-3:) a heavy chain comprising the amino acid sequence of SEQ ID NO:18 and a light chain comprising the amino acid sequence of SEQ ID NO:19; or
(PD1-4:) a heavy chain comprising the amino acid sequence of SEQ ID NO:20 and a light chain comprising the amino acid sequence of SEQ ID NO:21; or
(PD1-5:) a heavy chain comprising the amino acid sequence of SEQ ID NO:22 and a light chain comprising the amino acid sequence of SEQ ID NO:23.

Atezolizumab (Tecentriq, also known as MPDL3280A) is a phage-derived human IgG1k monoclonal antibody targeting PD-L1 and is described e.g. in Deng et al. mAbs 2016; 8:593-603. It has been approved by the FDA for the treatment of patients suffering from urothelial carcinoma.

Avelumab is a fully human anti-PD-L1 IgG1 monoclonal antibody and described in e.g. Boyerinas et al. Cancer Immunol. Res. 2015; 3:1148-1157.

Durvalumab (MEDI4736) is a human IgG1k monoclonal antibody with high specificity to PD-L1 and described in e.g. Stewart et al. Cancer Immunol. Res. 2015; 3:1052-1062 or in Ibrahim et al. Semin. Oncol. 2015; 42:474-483.

Further PD-1 antagonists disclosed by Li et al. (supra), or known to be in clinical trials, such as AMP-224, MEDI0680 (AMP-514), REGN2810, BMS-936559, JS001-PD-1, SHR-1210, BMS-936559, TSR-042, JNJ-63723283, MEDI4736, MPDL3280A, and MSB0010718C, may be used as alternative or in addition to the above mentioned antagonists.

The INNs as used herein are meant to also encompass all biosimilar antibodies having the same, or substantially the same, amino acid sequences as the originator antibody, including but not limited to those biosimilar antibodies authorized under 42 USC § 262 subsection (k) in the US and equivalent regulations in other jurisdictions.

PD-1 antagonists listed above are known in the art with their respective manufacture, therapeutic use and properties.

In one embodiment the PD-1 antagonist is pembrolizumab.

In another embodiment the PD-1 antagonist is nivolumab.

In another embodiment the PD-1 antagonist is pidilizumab.

In another embodiment the PD-1 antagonist is atezolizumab.

In another embodiment the PD-1 antagonist is avelumab.

In another embodiment the PD-1 antagonist is durvalumab.

In another embodiment the PD-1 antagonist is PDR-001.

In another embodiment the PD-1 antagonist is PD1-1.

In another embodiment the PD-1 antagonist is PD1-2.

In another embodiment the PD-1 antagonist is PD1-3.

In another embodiment the PD-1 antagonist is PD1-4.

In another embodiment the PD-1 antagonist is PD1-5.

Within this invention it is to be understood that the combinations, compositions, kits, methods, uses or compounds for use according to this invention may envisage the simultaneous, concurrent, sequential, successive, alternate or separate administration of the active agents or components. It will be appreciated that the bispecific binding molecule and the PD-1 antagonist can be administered formulated either dependently or independently, such as e.g. the bispecific binding molecule and the PD-1 antagonist may be administered either as part of the same pharmaceutical composition/dosage form or, preferably, in separate pharmaceutical compositions/dosage forms.

In this context, "combination" or "combined" within the meaning of this invention includes, without being limited, a product that results from the mixing or combining of more than one active agent and includes both fixed and non-fixed (e.g. free) combinations (including kits) and uses, such as e.g. the simultaneous, concurrent, sequential, successive, alternate or separate use of the components or agents. The term "fixed combination" means that the active agents are both administered to a patient simultaneously in the form of a single entity or dosage. The term "non-fixed combination" means that the active agents are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active agents.

The administration of the bispecific binding molecule/Compound A and the PD-1 antagonist/Compound B may take place by co-administering the active components or agents, such as e.g. by administering them simultaneously or concurrently in one single or in two separate formulations or dosage forms. Alternatively, the administration of the bispecific binding molecule and the PD-1 antagonist may take place by administering the active components or agents sequentially or in alteration, such as e.g. in two separate formulations or dosage forms.

For example, simultaneous administration includes administration at substantially the same time. This form of administration may also be referred to as "concomitant" administration. Concurrent administration includes administering the active agents within the same general time period, for example on the same day(s) but not necessarily at the same time. Alternate administration includes administration of one agent during a time period, for example over the course of a few days or a week, followed by administration of the other agent during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent during a second time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

Accordingly, in a preferred embodiment, in the method according the present invention, Compound A as described herein is administered simultaneously, concurrently, sequentially, successively, alternately or separately with Compound B as described herein. In a similar preferred embodiment, Compound A as described herein for use in a method according to the present invention, is administered simultaneously, concurrently, sequentially, successively, alternately or separately with Compound B as described herein. In a related preferred embodiment, Compound B, as described herein for use in a method according to the present invention, is administered simultaneously, concurrently, sequentially, successively, alternately or separately with Compound A as described herein. In a further preferred embodiment, the use of Compound A as described herein is provided wherein Compound A is to be administered simultaneously, concurrently, sequentially, successively, alternately or separately with Compound B. In a further related preferred embodiment, the use of Compound B as described herein is provided wherein Compound B is to be administered simultaneously, concurrently, sequentially, successively, alternately or separately with Compound A. In another embodiment, the kit according to the present invention is provided wherein the first pharmaceutical composition is to be administered simultaneously, concurrently, sequentially, successively, alternately or separately with the second pharmaceutical composition.

Preferred routes of administration for Compound A, Compound B, or both, administered separately or simultaneously, include, but are not limited to, oral, enterical, parenteral (e.g. intramuscular, intraperitoneal, intravenous, transdermal or subcutaneous injection, or implant), nasal, vaginal, rectal, or topical administration. In a preferred embodiment, the route of administration is intravenous administration, especially intravenous infusion or injection. The compounds of the present invention may be formulated, alone or together, in suitable dosage unit formulations containing conventional non-toxic pharmaceutically acceptable carriers, excipients and/or vehicles appropriate for each route of administration. More preferably, formulations include solid, semi-solid or liquid dosage forms, such as lyophilisation, liquid solutions (e.g. injectable and infusible solutions), dispersions or suspensions, liposomes and suppositories. The preferred mode depends on the intended mode of administration and therapeutic application. Especially preferred embodiments include liquid formulations and lyophilisation. In the case of a lyophilisation, the lyophilisate may be reconstituted in a liquid, preferably water.

The compounds as described herein may be administered daily, 5 times a week, 3 times a week, 2 times a week, once a week, once in 2 weeks, once in 3 weeks, once in 4 weeks. Preferable administration intervals include once a week and once in 2 weeks.

Preferably, Compounds A and B are administered once a week by i.v. infusion.

An administration regimen may include long-term treatment. By "long-term" is meant at least two weeks and preferably, several weeks, months or years of duration. Necessary modifications in this dosage regimen may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication. Administration may be daily, every second day, every third day, every fourth day, one day per week, two days per week, one day per two weeks, one day per three weeks, etc.

The compounds as described herein may be administered at therapeutically effective amounts in single or divided doses administered at appropriate time intervals. A therapeutically effective amount refers to an amount effective at dosages and for periods of time necessary to achieve the desired therapeutic result and is the minimum amount necessary to prevent, ameliorate, or treat a disease or disorder. A therapeutically effective amount of the compounds according to the present invention may vary according to factors such as the disease state, age, sex, and weight of the individual, and the ability of the compound to elicit a desired response in the individual. A therapeutically effective amount is also one in which any toxic or detrimental effects of the compound is outweighed by the therapeutically beneficial effects. A therapeutically effective dose preferably inhibits a measurable parameter, e.g. a tumor growth rate by at least about 20%, more preferably by at least about 40%, even more preferably by at least about 60%, and still more preferably by at least about 80% relative to untreated subjects or relative to a preceding untreated period of the same subject that is to be treated.

The active compounds may be administered in such doses which are therapeutically effective in monotherapy, or in such doses which are lower or higher than the doses used in monotherapy, but when combined result in a desired (jointly) therapeutically effective amount. The amount of the bispecific binding molecules of the invention required for use in treatment may be adapted to the particular binding molecule selected, the route of administration, the nature of the condition being treated and the age and condition of the patient and will be ultimately at the discretion of the attendant physician or clinician. Also, the dosage of the binding molecules of the invention may be adapted depending on the target cell, tumor, tissue, graft, or organ.

The desired dose of Compound A or Compound B may be administered as a fixed amount per administration or as bolus, to reach a set blood concentration in the patient.

Administration of Compound B, the PD-1 antagonist, as described herein may e.g. be by injection (e.g. subcutaneously or intravenously) at a dose of about 0.1 to 30 mg/kg of patient body weight, e.g. about 0.5 to 25 mg/kg of patient body weight, about 1 to 20 mg/kg of patient body weight, about 2 to 5 mg/kg of patient body weight, or about 3 mg/kg of patient body weight.

Dosages and therapeutic regimens of the PD-1 antagonist can be determined by a skilled artisan. Preferred dosage regimens for a PD-1 antagonist of the invention include 1 mg/kg of host body weight or 3 mg/kg of host body weight via intravenous administration, with the antibody being given using one of the following dosing schedules: (i) every four weeks for six dosages, then every three months; (ii) every three weeks; (iii) 3 mg/kg of host body weight once followed by 1 mg/kg of host body weight every three weeks. In certain embodiments, the PD-1 antagonist is administered by injection (e.g., subcutaneously or intravenously) at a dose of about 1 to 40 mg/kg of host body weight, e.g., 1 to 30 mg/kg of host body weight, e.g., about 5 to 25 mg/kg of host body weight, about 10 to 20 mg/kg of host body weight, about 1 to 5 mg/kg of host body weight, 1 to 10 mg/kg of host body weight, 5 to 15 mg/kg of host body weight, 10 to 20 mg/kg of host body weight, 15 to 25 mg/kg of host body weight, or about 3 mg/kg of host body weight. The dosing schedule can vary from e.g., once a week to once every 2, 3, or 4 weeks. In one embodiment, the PD-1 antagonist is administered at a dose from about 10 to 20 mg/kg of host body weight every other week. The antibody molecule can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the infusion rate of about 110 to 130 mg/m$^2$ achieves a level of about 3 mg/kg of host body weight. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the antibody is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The dosing schedule of Compound A and Compound B, separately or together, may vary from e.g. once a week to once every 2, 3 or 4 weeks. In a certain embodiment, the administered amount or dosage of Compound A, Compound B, or both, is lower (e.g. at least 20%, at least 30%, at least 40%, or at least 50% lower). In other embodiments, the amount or dosage of Compound A, Compound B, or both, that results in a desired effect (e.g. treatment of a hyperproliferative or oncological disease) is lower (e.g. at least 20%, at least 30%, at least 40%, or at least 50% lower).

The method, compounds, compounds for use, uses of compounds, pharmaceutical composition and kit according to the present invention comprises administering to the subject a combination of a bispecific antibody molecule and an anti-PD-1 antibody molecule as described herein.

Depending on the cancerous disease to be treated, the combination therapy as defined herein may be used on its own or in further combination with one or more additional therapeutic agents, in particular selected from chemotherapeutic agents or therapeutically active compounds that inhibit angiogenesis, signal transduction pathways or mitotic checkpoints in cancer cells.

The additional therapeutic agent may be administered simultaneously with, optionally as a component of the same pharmaceutical preparation, or before or after administration of the binding molecule and/or the PD1 antagonist.

The chemotherapeutic agent may be selected from hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortisone, fluoxymesterone, medroxyprogesterone, octreotide, arzoxifene, pasireotide, vapreotide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, pemetrexed, pyrimidine analogues like 5 fluorouracil, capecitabine, decitabine, nelarabine, and gemcitabine, purine and adenosine analogues such as mercaptopurine thioguanine, cladribine and pentostatin, cytarabine, fludarabine); antitumor antibiotics (e.g. anthracyclines like doxorubicin, daunorubicin, epirubicin and idarubicin, mitomycin-C, bleomycin dactinomycin, plicamycin, mitoxantrone, pixantrone, streptozocin); platinum derivatives (e.g. cisplatin, oxaliplatin, carboplatin, lobaplatin, satraplatin); alkylating agents (e.g. estramustine, meclorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. vinca alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan) and miscellaneous chemotherapeutics such as amifostine, anagrelide, interferone alpha, procarbazine, mitotane, and porfimer, bexarotene, celecoxib.

In a preferred embodiment, the treatment involving Compound A and Compound B further includes a "platinum doublet" therapy, i.e. therapy with (i) a platinum compound such as cisplatin or carboplatin, plus (ii) a third-generation chemotherapy agent such as docetaxel, paclitaxel, vinorelbine, or gemcitabine.

In another preferred embodiment, the treatment involving Compound A and Compound B is combined with a cancer cell targeting therapy.

In certain embodiments, the oncological or hyperproliferative disease, in particular cancer or a tumor disease, treated with the combination therapy as disclosed herein, includes but is not limited to, a solid tumor, a hematological cancer (e.g. leukemia, lymphoma, myeloma, e.g. multiple myeloma), and a metastatic lesion. In one embodiment, the cancer is a solid tumor. Examples of solid tumors include malignancies, e.g. sarcomas and carcinomas, e.g. adenocarcinomas of the various organ systems, such as those affecting the lung, breast, ovarian, lymphoid, gastrointestinal (e.g. colon), anal, genitals and genitourinary tract (e.g. renal, urothelial, bladder cells, prostate), pharynx, CNS (e.g. brain, neural or glial cells), head and neck, skin (e.g. melanoma) and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

As used herein, "hyperproliferative disease" refers to conditions wherein cell growth is increased over normal levels. For example, hyperproliferative diseases or disorders include malignant diseases (e.g. esophageal cancer, colon cancer, biliary cancer) and non-malignant diseases (e.g. atherosclerosis, benign hyperplasia, benign prostatic hypertrophy).

In one embodiment, the cancer is chosen from a lung cancer (e.g. NSCLC (e.g. a NSCLC with squamous and/or non-squamous histology, or a NSCLC adenocarcinoma)), a melanoma (e.g. an advanced melanoma), a renal cancer (e.g. a renal cell carcinoma), a liver cancer, a myeloma (e.g. a multiple myeloma), a prostate cancer, a breast cancer (e.g. a breast cancer that does not express one, two or all of estrogen receptor, progesterone receptor, or Her2/neu, e.g. a triple negative breast cancer), a colorectal cancer, a pancreatic cancer, a head and neck cancer (e.g. head and neck squamous cell carcinoma (HNSCC), anal cancer, gastroesophageal cancer, thyroid cancer, cervical cancer, a lymphoproliferative disease (e.g. a post-transplant lymphoproliferative disease) or a hematological cancer, T-cell lymphoma, B-cell lymphoma, a non-Hodgkin lymphoma, or a leukemia (e.g. a myeloid leukemia or a lymphoid leukemia).

In another embodiment, the cancer is chosen from a carcinoma (e.g. advanced or metastatic carcinoma), melanoma or a lung carcinoma, e.g. a NSCLC.

In one embodiment, the cancer is a lung cancer, e.g. a NSCLC or small cell lung cancer. In a preferred embodiment, the cancer is NSCLC.

In an especially preferred embodiment combinable with any aspect and embodiment of the invention, the combination therapy according to the present invention is for treating a patient suffering from locally advanced or metastatic non-squamous NSCLC without EGFR mutation or ALK translocation. Therein, optionally, the patient is selected according to his/her PD-L1 expression status, such as high or low PD-L1 expression status. The treatment may be a first line treatment, i.e. the first treatment given for the disease (NSCLC). Accordingly the patient may not have undergone chemotherapy or radiation therapy, in particular not for the treatment of NSCLC when treated according to the invention. By determining the PD-L1 expression status prior to any cancer treatment of the patient, reliable results can be achieved.

PD-L1 expression status can be determined as described by Han et al. (Journal of Pathology and Translational Medicine 2017; 51: 40-48) or by Wang et al. (OncoTargets and Therapy 2016:95023-5039), such as by using immunohistochemistry. A biopsy sample of the tumor of the patient to be treated may be used for PD-L1 expression status determination. A single tumor biopsy or multiple biopsies from an individual patient may be used, in case of more than one biopsies used, preferably the biopsy with the highest PD-L1 expression is used to determined PD-L1 expression status according to the invention. PD-L1 can be determined on cell surface (membranous) or cytoplasmic expression, expression by tumor cells only and/or by other cells in the tumor milieu (e.g. immune cells). The thresholds for considering PD-L1 positive expression can be e.g. at least 1%, at least 5% or at least 10% PD-L1 expression in cells, e.g. tumor and/or immune cells, wherein samples with ≥1%, ≥5% or ≥10% PD-L1 expression in cells, e.g. as determined by immunohistochemistry can be considered PD-L1 "positive". In a preferred embodiment, the PD-L1 expression status is determined on tumor cells or immune cells, more preferably on tumor cells, wherein a PD-L1 expression of 1% to 5% of cells is considered low PD-L1 expression and a PD-L1 expression of >5% of cells, e.g. >5% to 40% of cells, is considered as high PD-L1 expression, as above preferably by determination by immunohistochemistry, e.g. as described by Han et al. or Wang et al. Patients to be treated may be patients with low PD-L1 expression, patients with high PD-L1 expression, patients with low PD-L1 expression excluding patients with high PD-L1 expression or patients with high PD-L1 expression excluding patients with low PD-L1 expression.

In one embodiment, the cancer is a melanoma, e.g. an advanced melanoma. In one embodiment, the cancer is an advanced or unresectable melanoma that does not respond to other therapies. In other embodiments, the cancer is a melanoma with a BRAF mutation (e.g. a BRAF V600 mutation).

In another embodiment, the cancer is a hepatocarcinoma, e.g. an advanced hepatocarcinoma, with or without a viral infection, e.g. a chronic viral hepatitis.

In another embodiment, the cancer is a prostate cancer, e.g. an advanced prostate cancer.

In yet another embodiment, the cancer is a myeloma, e.g. multiple myeloma.

In yet another embodiment, the cancer is a renal cancer, e.g. a renal cell carcinoma (RCC) (e.g. a metastatic RCC or clear renal cell carcinoma (CCRCC)).

As outlined above, the present invention relates to a pharmaceutical composition comprising Compound A and Compound B as defined herein and to a kit comprising a first pharmaceutical composition comprising Compound A as defined herein and to a second pharmaceutical composition comprising Compound B as defined herein.

The term "pharmaceutical composition" as defined herein refers to a preparation which is in such form as to permit the biological activity of an active ingredient contained therein to be effective, and which contains no additional components which are unacceptably toxic to a subject to which the composition would be administered. A pharmaceutical composition of the present invention can be administered by a variety of methods known in the art. As will be appreciated by the skilled artisan, the route and/or mode of administration will vary depending upon the desired results.

Regardless of the route of administration selected, the Compounds used in a combination therapy of the present invention and/or the pharmaceutical composition, the first pharmaceutical composition and the second pharmaceutical composition of the present invention, are formulated into pharmaceutically acceptable dosage forms by conventional methods known to those of skill in the art.

The kit as defined herein may comprise a suitable container or several suitable containers comprising the first pharmaceutical composition and/or the second pharmaceutical composition, wherein the first and the second pharmaceutical composition may be contained in the same container or in different containers. The kit may be used in any method or any uses of the invention.

Preferably, the kit according to the present invention further comprises a package insert comprising readable instructions for using Compound A and/or Compound B in the treatment and/or prevention of an oncological or hyperproliferative disease, preferably cancer or a tumor disease, especially NSCLC, in a patient in need thereof. The instructions may provide further detailed as described above with regard to the inventive method and any of its preferred embodiments.

The use of the word "a" or "an" when used in conjunction with the term "comprising" in the claims and/or the specification may mean "one", but it is also consistent with the meaning of "one or more", "at least one", and "one or more than one".

"About" as used herein means an acceptable degree of error for the quantity measured given the nature of precision of the measurements. Exemplary degrees of error are within 20%, typically within 10%, and more typically within 5% of a given value or range of values.

The term "treating" or "treatment" as used herein means to cure an already present disease state or condition or to increase the likelihood of recovery from the disease state or condition. Treating can also include inhibiting, i.e. arresting the development of a disease state or condition, and ameliorating, i.e. causing regression or delaying progression of a disease. Treatment can be to ameliorate disease symptoms without curing a patient.

The term "preventing" or "prevention" as used herein does not mean to stop a disease state or condition from occurring in a patient or subject completely but may also refer to a reduced risk of developing a disease state or condition.

The present invention is further illustrated by the following examples, without being necessarily limited to these embodiments of the invention. An example or part thereof, including compounds, doses and administration routes, as well as treatment combinations, each as such or in combination with the detailed description above forms part of the invention.

EXAMPLES

Acronyms and Abbreviations

CD Cluster of differentiation
DMEM Dulbecco's Modified Eagle Medium
FCS Fetal calf serum
ID Identifier
i.p. intraperitoneal
LAG-3 Lymphocyte activation gene 3

M Molar
MEM Minimum Essential Media
PBS Phosphate buffered saline
PD-1 Programmed cell death 1
PD-L1 Programmed cell death ligand 1
PD-L2 Programmed cell death ligand 2
q3or4d every $3^{rd}$ or $4^{th}$ day (twice weekly)
R Response
TGI Tumour Growth Inhibition, calculated to the formula:

$$TGI=100\times\{1-[(treated_{final\ day}-treated_{day1})/(control_{final\ day}-control_{day1})]\}$$

TIL Tumour infiltrating lymphocytes

Example 1

Test Compounds

A rat IgG2a anti-murine PD-1 antibody EX101359 (clone RMP1-14) (10 mg/kg), the bispecific, VEGF and Ang2 binding protein VEGFANGBII22 (having a structure/sequence as defined hereinabove and in SEQ ID NOs:11, 12 and 13), the small molecule TKI vatalanib and the CrossMab antibody vanucizumab (anti-human VEGF-A and anti-human/murine Ang-2) were used for these experiments. For the control group the corresponding Isotype to the PD-1 antibody Rat IgG2a (EX101362) was used (10 mg/kg), i.e. an antibody which has a similar sequence but does not bind to PD-1. All antibodies were diluted in 1×PBS and were ordered from BioXcell, West Lebanon, N.H., USA.

Cells

LL/2(LLC1) is a murine lung carcinoma cell line, which was bought from American Type Culture Collection (ATCC), USA (CRL-1642). Cells were cultured in T175 tissue culture flasks at 37° C. and 5% $CO_2$. The medium used was DMEM supplemented with 10% FCS (HyClone® Fetal Bovine Serum Characterized; Cat No SH30071.03; by Thermo Scientific). Cultures were split every two-three days with a ratio of 1:4/1:6.

Mice

The C57BL/6NTac is a fully immune competent mouse strain, which was supplied by Taconic Denmark. Female mice were shipped from Taconic at an age of 7 weeks to a local animal facility. After arrival at the animal facility, mice were allowed to adjust to conditions at least for 5 days before they were used for experiments. They were housed in groups of 10 under standardized conditions at 21.5+/−1.5 C temperature and 55+/−10% humidity. Standardized diet (PROVIMI KLIBA) and autoclaved tap water were provided ad libitum. Subcutaneous microchips implanted under isoflurane anesthesia were used to identify each mouse. Cage cards showing the study number, the animal identification number, the antibody and compound and dose levels, the administration route as well as the schedule remained with the animals throughout the study.

Establishment of Tumors, Randomization

The animals were dispatched randomly by the computer program SEPIA into the different groups. To establish the subcutaneous tumor model, LL/2 cells were harvested, resuspended in PBS/5% FCS and mixed 1:2 with Matrigel® Matrix (without growth factors, Corning, Tewksbury, Mass., USA) at $5\times10^5$/ml. 100 µl cell suspension containing $5\times10^4$ cells were injected per mouse (day-5).

Administration of Test Compound

Antibodies were diluted in PBS to 1 mg/mL and injected intraperitoneally with a volume of 10 ml/kg. Dilution was kept at 4° C. for a maximum of 5 days. Start of treatment (day 1) was 3 days post cell injection. Vatalanib was suspended in a 5% Natrosol™ hydroxyethylcellulose solution and administered intragastrally by gavage needle (Infusionskanüle Olive A, Acufirm, No. 146411-1). The administration volume was 10 ml per kg body weight. Administration was once every 24 h. To prepare the suspension, compound was added to the Natrosol™ hydroxyethylcellulose solution and the mixture was stirred overnight. Sometimes ultrasonication was needed. Solutions were kept at room temperature in the dark for a maximum of 1 week.

TABLE 2

Treatment groups

| Group | No. of mice | Treatment compound(s) | Dose [mg/kg] | Schedule | Route |
|---|---|---|---|---|---|
| 1 | 10 | Isotype PD-1 antibody (EX101362) | 10 mg/kg | q3or4d | i.p. |
| 2 | 10 | anti-murine PD-1 antibody (EX101359) | 10 mg/kg | q3or4d | i.p. |
| 3 | 10 | VEGFANGBII22 | 15 mg/kg | q3or4d | i.p. |
| 4 | 10 | Vatalanib (EXBF003) | 100 mg/kg | qd | po |
| 5 | 10 | anti-murine PD-1 antibody (EX101359); VEGFANGBII22; Vatalanib (EXBF003) | 10 mg/kg, 15 mg/kg, 100 mg/kg | q3or4d, qd | i.p., p.o. |
| 6 | 10 | anti-VEGF/Ang2 antibody (vanucizumab); | 15 mg/kg | q3or4d | i.p. |
| 7 | 10 | anti-murine PD-1 antibody (EX101359); anti-VEGF/Ang2 antibody (vanucizumab); Vatalanib (EXBF003) | 10 mg/kg, 15 mg/kg, 100 mg/kg | q3or4d, qd | i.p., p.o. |

Monitoring Tumor Growth and Disease Progression

Tumor diameters were measured three times a week (Monday, Wednesday and Friday) with a caliper. From day 14 until day 28 after the start of treatment, all tumors were measured daily. The volume of each tumor [in $mm^3$] was calculated according to the formula "tumor volume=length*$diameter^2$*pi/6." To monitor side effects of treatment, mice were inspected daily for abnormalities and body weight was determined at least three times a week. Animals were sacrificed when the tumors reached a size of 1500 $mm^3$ or a tumor necrosis was bigger than ⅓ of the tumour surface. In addition, animals with a body weight loss >18% were euthanized for ethical reasons. Tumor growth inhibition (TGI) values were calculated as follows:

$$TGI=100\times\{1-[(treated_{final\ day}-treated_{day1})/(control_{final\ day}-control_{day1})]\}$$

Statistical Analysis—Anti-Tumor Efficacy

For the evaluation of the statistical significance of tumor inhibition a one-tailed nonparametric Mann-Whitney-Wilcoxon U-test was performed, based on the hypothesis that an effect would only be measurable in one direction (i.e. expectation of tumor inhibition but not tumor stimulation). In this case, the U-test compares the ranking of the individual tumors of two groups, according to the absolute volume on a particular day (pairwise comparisons between groups). Analysis was performed on day 17 of the experiment. The p-values obtained from the U-test were adjusted using the Bonferroni-Holm correction. By convention, p-values ≤0.05 indicate significance of differences.

Results

Mice in the isotope control group were treated twice weekly with EX101362 intraperitoneally. During the treatment period tumors grew from a median volume of 41 mm³ to a volume of 1275 mm³. Treatment with 10 mg/kg EX101359, the anti-murine PD-1 antibody, was administered twice weekly intraperitoneally. EX101359-treatment reduced tumour growth compared to the isotype control (median TGI=51%).

Treatment with VEGFANGBII22 alone resulted in a TGI of 49%. Treatment with vatalanib alone resulted in a TGI of 54%. The combined treatment with vatalanib, VEGFANGBII22 and anti-PD1 resulted in a TGI of 79%.

Treatment with vanucizumab alone resulted in a TGI of 64%. The combined treatment with vatalanib, vanucizumab and anti-PD1 resulted in a TGI of 81%.

Further results of the combination and results of comparative compounds are shown in FIG. 1.

Conclusion

In this study the monotherapies of anti-PD1, vatalanib (targeting VEGFR), VEGFANGBII22 and vanucizumab showed a minimal to medium anti-tumor response with TGI values of 51%, 54%, 49% and 64%, respectively. The triple drug combinations of anti-PD1 plus vatalanib plus VEGFANGBII22 or anti-PD1 plus vatalanib plus vanucizumab were clearly more effective with TGI values of 79% and 81%. By analyzing the response curves of the individual tumors the triple drug combination of anti-PD1 plus vatalanib plus VEGFANGBII22 stand out as one of the treated tumors shows shrinkage whereas all tumors in the anti-PD1 plus vatalanib plus vanucizumab treated group show reduced tumor growth.

The triple drug combinations show a better anti-tumor effect compared to the isotype control and the monotherapies. The triple drug combination of anti-PD1 plus vatalanib plus the VEGFANGBII22 even induced tumor shrinkage in one treated individual. All treatments were well tolerated in this experiment.

It should be understood from the above that upon transferring these results to a therapy in humans, the compound VEGFANGBII22 will include an anti-Ang2 as well as an anti-VEGF activity, as this compound is binding to human VEGF. Thus, additional use of an anti-VEGF agent such as vatalanib in the above-described experiment will not be required. Thus, the above data indicate that treatment of humans with VEGFANGBII22 plus a PD1 antagonist, such as an anti-PD1 antibody, will bring about useful therapeutic effects in human patients.

Example 2

A further experiment was set up essentially as described in Example 1, comparing monotherapies with the triple drug combination VEGFANGBII22 plus anti-PD1 antibody plus vatalanib (with vatalanib again mimicking the anti-VEGF activity in mice, which activity cannot be expected from VEGFANGBII22 because the VEGF binding component of that compound does not bind to mouse VEGF).

Again, TGI values were determined, with 80% being achieved upon administration of the triple combination. In contrast thereto, TGI values of 22% (anti-PD-1 antibody), 27% (anti-Ang2 activity of VEGFANGBII22) and 43% (vatalanib) have been achieved by the monotherapies.

Additionally, survival of the mice within the respective treatment group has been determined. As can be seen from FIG. 2, only treatment with VEGFANGBII22, vatalanib and the PD1 antagonist provided for survivals significantly beyond the 30 days limit. Again, this shows that the proposed treatment may be expected to achieve superior effects also in humans (again being understood that the anti-VEGF activity will already be provided by the VEGFANGBII22 component, so that no addition of vatalanib will be required).

The invention claimed is:

1. A method of treating a solid tumor cancer comprising administering to a patient in need thereof
   a. a therapeutically effective amount of a Compound A and
   b. a therapeutically effective amount of a Compound B, wherein Compound A is a binding molecule comprising a VEGF-binding immunoglobulin single variable domain, a serum albumin binding immunoglobulin single variable domain, and an Ang2-binding immunoglobulin single variable domain wherein said VEGF-binding immunoglobulin single variable domain has the following CDR sequences:

```
CDR1:
                                        (SEQ ID NO: 1)
SYSMG,

CDR2:
                                        (SEQ ID NO: 2)
AISKGGYKYDAVSLEG,

CDR3:
                                        (SEQ ID NO: 3)
SRAYGSSRLRLADTYEY;
``` said serum albumin binding immunoglobulin single variable domain has the following CDR sequences:

```
CDR1:
                                        (SEQ ID NO: 4)
SFGMS,

CDR2:
                                        (SEQ ID NO: 5)
SISGSGSDTLYADSVKG,

CDR3:
                                        (SEQ ID NO: 6)
GGSLSR;
``` said Ang2-binding immunoglobulin single variable domain has the following CDR sequences:

```
CDR1:
                                        (SEQ ID NO: 7)
DYAIG,

CDR2:
                                        (SEQ ID NO: 8)
AIRSSGGSTYYADSVKG,

CDR3:
                                        (SEQ ID NO: 9)
VPAGRLRYGEQWYPIYEYDA;
``` wherein each single variable domain is separated by a linker peptide; and wherein Compound B is a PD-1 antagonist antibody selected from the group consisting of pembrolizumab, nivolumab, pidilizumab, PD1-1 (HC/LC; SEQ ID NO: 14, 15), PD1-2 (HC/LC; SEQ ID NO: 16, 17), PD1-3 (HC/LC; SEQ ID NO: 18, 19), PD1-4 (HC/LC; SEQ ID NO: 20, 21), and PD1-5 (HC/LC; SEQ ID NO: 22, 23).

2. The method according to claim 1, wherein the solid tumor cancer is lung cancer.

3. The method according to claim 1, wherein the solid tumor cancer is non-small cell lung cancer (NSCLC).

4. The method according to claim 1, wherein said immunoglobulin single variable domains of Compound A are VHH domains.

5. The method according to claim 1, wherein Compound A has the amino acid sequence according to SEQ ID NO: 11, SEQ ID NO:12, or SEQ ID NO:13, wherein each single variable domain is separated by a linker peptide.

6. The method according to claim 1, wherein Compound A is administered simultaneously, concurrently, sequentially, successively, alternately or separately with Compound B.

* * * * *

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: CDR sequence

<400> SEQUENCE: 1

Ser Tyr Ser Met Gly
1               5

<210> SEQ ID NO 2
<211> LENGTH: 16
<212> TYPE: PRT
<213> ORGANISM: Artificial Sequence
<220> FEATURE:
<223> OTHER INFORMATION: CDR sequence

<400> SEQUENCE: 2

Ala Ile Ser Lys Gly Gly Tyr Lys Tyr Asp Ala Val Ser Leu Glu Gly
1               5                   10                  15

<210> SEQ ID NO 3
<211> LENGTH: 17
<212> TYPE: PRT
<213> ORGANISM: Artificial Sequence
<220> FEATURE:
```

<223> OTHER INFORMATION: CDR sequence

<400> SEQUENCE: 3

Ser Arg Ala Tyr Gly Ser Ser Arg Leu Arg Leu Ala Asp Thr Tyr Glu
1               5                   10                  15

Tyr

<210> SEQ ID NO 4
<211> LENGTH: 5
<212> TYPE: PRT
<213> ORGANISM: Artificial Sequence
<220> FEATURE:
<223> OTHER INFORMATION: CDR sequence

<400> SEQUENCE: 4

Ser Phe Gly Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: CDR sequence

<400> SEQUENCE: 5

Ser Ile Ser Gly Ser Gly Ser Asp Thr Leu Tyr Ala Asp Ser Val Lys
1               5                   10                  15

Gly

<210> SEQ ID NO 6
<211> LENGTH: 6
<212> TYPE: PRT
<213> ORGANISM: Artificial Sequence
<220> FEATURE:
<223> OTHER INFORMATION: CDR sequence

<400> SEQUENCE: 6

Gly Gly Ser Leu Ser Arg
1               5

<210> SEQ ID NO 7
<211> LENGTH: 5
<212> TYPE: PRT
<213> ORGANISM: Artificial Sequence
<220> FEATURE:
<223> OTHER INFORMATION: CDR sequence

<400> SEQUENCE: 7

Asp Tyr Ala Ile Gly
1               5

<210> SEQ ID NO 8
<211> LENGTH: 17
<212> TYPE: PRT
<213> ORGANISM: Artificial Sequence
<220> FEATURE:
<223> OTHER INFORMATION: CDR sequence

<400> SEQUENCE: 8

Ala Ile Arg Ser Ser Gly Gly Ser Thr Tyr Tyr Ala Asp Ser Val Lys
1               5                   10                  15

Gly

```
<210> SEQ ID NO 9
<211> LENGTH: 20
<212> TYPE: PRT
<213> ORGANISM: Artificial Sequence
<220> FEATURE:
<223> OTHER INFORMATION: CDR sequence

<400> SEQUENCE: 9

Val Pro Ala Gly Arg Leu Arg Tyr Gly Glu Gln Trp Tyr Pro Ile Tyr
1               5                   10                  15

Glu Tyr Asp Ala
            20

<210> SEQ ID NO 10
<211> LENGTH: 5
<212> TYPE: PRT
<213> ORGANISM: Artificial Sequence
<220> FEATURE:
<223> OTHER INFORMATION: binding motif peptide sequence

<400> SEQUENCE: 10

Met Tyr Pro Pro Tyr
1               5

<210> SEQ ID NO 11
<211> LENGTH: 387
<212> TYPE: PRT
<213> ORGANISM: Artificial Sequence
<220> FEATURE:
<223> OTHER INFORMATION: bispecific anti-VEGF-anti-Ang2 binding
      molecules

<400> SEQUENCE: 11

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Phe Val
        35                  40                  45

Val Ala Ile Ser Lys Gly Gly Tyr Lys Tyr Asp Ala Val Ser Leu Glu
    50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
```

```
                    210                 215                 220
Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Leu Val Gln Pro
            260                 265                 270

Gly Gly Ser Leu Arg Leu Ser Cys Ala Val Ser Gly Ile Thr Leu Asp
            275                 280                 285

Asp Tyr Ala Ile Gly Trp Phe Arg Gln Ala Pro Gly Lys Glu Arg Glu
            290                 295                 300

Gly Val Ser Ala Ile Arg Ser Ser Gly Gly Ser Thr Tyr Tyr Ala Asp
305                 310                 315                 320

Ser Val Lys Gly Arg Phe Thr Ile Ser Ser Asp Asn Ser Lys Asn Thr
                325                 330                 335

Val Tyr Leu Gln Met Asn Ser Leu Arg Pro Glu Asp Thr Ala Val Tyr
                340                 345                 350

Tyr Cys Ala Ala Val Pro Ala Gly Arg Leu Arg Leu Tyr Gly Glu Gln Trp
            355                 360                 365

Tyr Pro Ile Tyr Glu Tyr Asp Ala Trp Gly Gln Gly Thr Leu Val Thr
            370                 375                 380

Val Ser Ser
385

<210> SEQ ID NO 12
<211> LENGTH: 387
<212> TYPE: PRT
<213> ORGANISM: Artificial Sequence
<220> FEATURE:
<223> OTHER INFORMATION: bispecific anti-VEGF-anti-Ang2 binding
      molecules

<400> SEQUENCE: 12

Glu Val Gln Leu Val Glu Ser Gly Gly Gly Leu Val Gln Pro Gly Gly
1                   5                   10                  15

Ser Leu Arg Leu Ser Cys Ala Ala Ser Gly Arg Thr Phe Ser Ser Tyr
                20                  25                  30

Ser Met Gly Trp Phe Arg Gln Ala Pro Gly Lys Glu Arg Glu Phe Val
            35                  40                  45

Val Ala Ile Ser Lys Gly Gly Tyr Lys Tyr Asp Ala Val Ser Leu Glu
        50                  55                  60

Gly Arg Phe Thr Ile Ser Arg Asp Asn Ala Lys Asn Thr Val Tyr Leu
65                  70                  75                  80

Gln Ile Asn Ser Leu Arg Pro Glu Asp Thr Ala Val Tyr Tyr Cys Ala
                85                  90                  95

Ser Ser Arg Ala Tyr Gly Ser Ser Arg Leu Arg Leu Ala Asp Thr Tyr
            100                 105                 110

Glu Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175
```

```
Lys Gly Leu Glu Trp Val Ser Ser Ile Ser Gly Ser Gly Ser Asp Thr
                180                 185                 190
Leu Tyr Ala Asp Ser Val Lys Gly Arg Phe Thr Ile Ser Arg Asp Asn
            195                 200                 205
Ala Lys Thr Thr Leu Tyr Leu Gln Met Asn Ser Leu Arg Pro Glu Asp
        210                 215                 220
Thr Ala Val Tyr Tyr Cys Thr Ile Gly Gly Ser Leu Ser Arg Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Gly Leu Val Gln Pro
            260                 265                 270
Gly Gly Ser Leu Arg Leu Ser Cys Ala Val Ser Gly Ile Thr Leu Asp
        275                 280                 285
Asp Tyr Ala Ile Gly Trp Phe Arg Gln Ala Pro Gly Lys Glu Arg Glu
        290                 295                 300
Gly Val Ser Ala Ile Arg Ser Ser Gly Gly Ser Thr Tyr Tyr Ala Asp
305                 310                 315                 320
Ser Val Lys Gly Arg Phe Thr Ile Ser Ser Asp Asn Ser Lys Asn Thr
                325                 330                 335
Val Tyr Leu Gln Met Asn Ser Leu Arg Pro Glu Asp Thr Ala Val Tyr
            340                 345                 350
Tyr Cys Ala Ala Val Pro Ala Gly Arg Leu Arg Tyr Gly Glu Gln Trp
        355                 360                 365
Tyr Pro Ile Tyr Glu Tyr Asp Ala Trp Gly Gln Gly Thr Leu Val Thr
        370                 375                 380
Val Ser Ser
385

<210> SEQ ID NO 13
<211> LENGTH: 386
<212> TYPE: PRT
<213> ORGANISM: Artificial Sequence
<220> FEATURE:
<223> OTHER INFORMATION: bispecific anti-VEGF-anti-Ang2 binding
      molecules

<400> SEQUENCE: 13

Val Gln Leu Val Glu Ser Gly Gly Gly Leu Val Gln Pro Gly Gly Ser
1               5                   10                  15
Leu Arg Leu Ser Cys Ala Ala Ser Gly Arg Thr Phe Ser Ser Tyr Ser
            20                  25                  30
Met Gly Trp Phe Arg Gln Ala Pro Gly Lys Glu Arg Glu Phe Val Val
        35                  40                  45
Ala Ile Ser Lys Gly Gly Tyr Lys Tyr Asp Ala Val Ser Leu Glu Gly
    50                  55                  60
Arg Phe Thr Ile Ser Arg Asp Asn Ala Lys Asn Thr Val Tyr Leu Gln
65                  70                  75                  80
Ile Asn Ser Leu Arg Pro Glu Asp Thr Ala Val Tyr Tyr Cys Ala Ser
                85                  90                  95
Ser Arg Ala Tyr Gly Ser Ser Arg Leu Arg Leu Ala Asp Thr Tyr Glu
            100                 105                 110
Tyr Trp Gly Gln Gly Thr Leu Val Thr Val Ser Ser Gly Gly Gly Gly
        115                 120                 125
Ser Gly Gly Gly Ser Glu Val Gln Leu Val Glu Ser Gly Gly Gly Leu
    130                 135                 140
```

```
Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Arg Ser Ser Gln
225                 230                 235                 240

Gly Thr Leu Val Thr Val Ser Ser Gly Gly Gly Gly Ser Gly Gly Gly
                245                 250                 255

Ser Glu Val Gln Leu Val Glu Ser Gly Gly Gly Leu Val Gln Pro Gly
                260                 265                 270

Gly Ser Leu Arg Leu Ser Cys Ala Val Ser Gly Ile Thr Leu Asp Asp
            275                 280                 285

Tyr Ala Ile Gly Trp Phe Arg Gln Ala Pro Gly Lys Glu Arg Glu Gly
        290                 295                 300

Val Ser Ala Ile Arg Ser Ser Gly Gly Ser Thr Tyr Tyr Ala Asp Ser
305                 310                 315                 320

Val Lys Gly Arg Phe Thr Ile Ser Ser Asp Asn Ser Lys Asn Thr Val
                325                 330                 335

Tyr Leu Gln Met Asn Ser Leu Arg Pro Glu Asp Thr Ala Val Tyr Tyr
                340                 345                 350

Cys Ala Ala Val Pro Ala Gly Arg Leu Arg Tyr Gly Glu Gln Trp Tyr
            355                 360                 365

Pro Ile Tyr Glu Tyr Asp Ala Trp Gly Gln Gly Thr Leu Val Thr Val
        370                 375                 380

Ser Ser
385

<210> SEQ ID NO 14
<211> LENGTH: 446
<212> TYPE: PRT
<213> ORGANISM: Artificial Sequence
<220> FEATURE:
<223> OTHER INFORMATION: HC of PD1-1

<400> SEQUENCE: 14

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110
```

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly
    435                 440                 445

<210> SEQ ID NO 15
<211> LENGTH: 218
<212> TYPE: PRT
<213> ORGANISM: Artificial Sequence
<220> FEATURE:
<223> OTHER INFORMATION: LC of PD1-1

<400> SEQUENCE: 15

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

```
Gly Ile Ser Phe Met Asn Trp Tyr Gln Gln Lys Pro Gly Gln Ala Pro
            35                  40                  45

Lys Leu Leu Ile Tyr Val Ala Ser Asn Gln Gly Ser Gly Ile Pro Ala
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 16
<211> LENGTH: 446
<212> TYPE: PRT
<213> ORGANISM: Artificial Sequence
<220> FEATURE:
<223> OTHER INFORMATION: HC of PD1-2

<400> SEQUENCE: 16

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Pro Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 17
<211> LENGTH: 218
<212> TYPE: PRT
<213> ORGANISM: Artificial Sequence
<220> FEATURE:
<223> OTHER INFORMATION: LC of PD1-2

<400> SEQUENCE: 17

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95
```

```
Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 18
<211> LENGTH: 446
<212> TYPE: PRT
<213> ORGANISM: Artificial Sequence
<220> FEATURE:
<223> OTHER INFORMATION: HC of PD1-3

<400> SEQUENCE: 18

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 19
<211> LENGTH: 218
<212> TYPE: PRT
<213> ORGANISM: Artificial Sequence
<220> FEATURE:
<223> OTHER INFORMATION: LC of PD1-3

<400> SEQUENCE: 19

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 20
<211> LENGTH: 446
<212> TYPE: PRT
<213> ORGANISM: Artificial Sequence
<220> FEATURE:
<223> OTHER INFORMATION: HC of PD1-4

<400> SEQUENCE: 20

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
            35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly
            435                 440                 445

<210> SEQ ID NO 21
<211> LENGTH: 218
<212> TYPE: PRT
<213> ORGANISM: Artificial Sequence
<220> FEATURE:
<223> OTHER INFORMATION: LC of PD1-4

<400> SEQUENCE: 21

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 22
<211> LENGTH: 446
<212> TYPE: PRT
<213> ORGANISM: Artificial Sequence
<220> FEATURE:
<223> OTHER INFORMATION: HC of PD1-5

<400> SEQUENCE: 22

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
                435                 440                 445

<210> SEQ ID NO 23
<211> LENGTH: 218
<212> TYPE: PRT
<213> ORGANISM: Artificial Sequence
<220> FEATURE:
<223> OTHER INFORMATION: LC of PD1-5

<400> SEQUENCE: 23

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
                20                  25                  30

Gly Ile Ser Phe Met Asn Trp Tyr Gln Gln Lys Pro Gly Gln Ala Pro
            35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```